United States Patent [19]

Kelley et al.

[11] Patent Number: 5,874,407
[45] Date of Patent: Feb. 23, 1999

[54] FACTOR VIIA INHIBITORS

[75] Inventors: Robert F. Kelley, San Bruno; Robert A. Lazarus, Millbrae; Geoffrey F. Lee, Pacifica, all of Calif.

[73] Assignee: Genentech, Inc., South San Francisco, Calif.

[21] Appl. No.: 932,589

[22] Filed: Sep. 17, 1997

Related U.S. Application Data

[62] Division of Ser. No. 566,800, Dec. 4, 1995, abandoned.

[51] Int. Cl.$^6$ .......................... A61K 38/00; C12P 21/06; C12P 21/04
[52] U.S. Cl. ........................ 514/12; 435/69.1; 435/69.2; 435/69.7
[58] Field of Search ................................ 435/69.1, 69.7, 435/69.2; 514/12, 822

[56] References Cited

U.S. PATENT DOCUMENTS

| | | | |
|---|---|---|---|
| 5,312,736 | 5/1994 | Rasmussen et al. | 435/69.2 |
| 5,346,991 | 9/1994 | Roy et al. | 530/350 |
| 5,416,093 | 5/1995 | Shuman | 514/307 |
| 5,434,073 | 7/1995 | Dawson et al. | 435/216 |

FOREIGN PATENT DOCUMENTS

| | | |
|---|---|---|
| 439442 | 7/1991 | European Pat. Off. . |
| WO 91/02750 | 3/1991 | WIPO . |
| WO 91/02753 | 3/1991 | WIPO . |
| WO 93/14119 | 7/1993 | WIPO . |
| WO 94/01461 | 1/1994 | WIPO . |
| WO 94/12637 | 6/1994 | WIPO . |
| WO 94/27631 | 12/1994 | WIPO . |
| WO 94/28017 | 12/1994 | WIPO . |
| WO 95/23860 | 9/1995 | WIPO . |

OTHER PUBLICATIONS

Altman et al., "Intracellular expression of BPTI fusion proteins and single column cleavage/affinity purification by chymotrypsin" *Protein Eng.* 4:593–600 (1991).
Auerswald et al., "Expression, Isolation and Characterization of Recombinant [Arg$^{15}$,Glu$^{52}$] Aprotinin" *Biol. Chem. Hoppe–Seyler* 369:27–35 (1988).
Bach, Ronald R., "Initiation of Coagulation by Tissue Factor" *CRC Critical Reviews in Biochemistry* 23(4):339–368 (1988).
Badimon et al., "Hirudin and Other Thrombin Inhibitors; Experimental Results and Potential Clinical Applications" *TCM* 1(6):261–267 (1991).
Beckmann, J. et al., "Preparation of chemically 'mutated' aprotinin homologues by semisynthesis" *European Journal of Biochemistry* 176:675–682 (1988).
Bode, W. et al., "Natural protein proteinase inhibitors and their interaction with proteinases" *European Journal of Biochemistry* 204:433–451 (1992).
Bone, R.C., "Modulators of Coagulation: A Critical Appraisal of Their Role In Sepsis" *Arch Intern Med* 152:1381–1389 (1992).

Bromberg et al., "Tissue factor promotes melanoma metastasis by a pathway independent of blood coagulation" *Proc. Natl. Acad. Sci. USA* 92:8205–8209 (1995).
Broze, Jr. et al., "The Lipoprotein–Associated Coagulation Inhibitor That Inhibits the Factor VII–Tissue Factor Complex Also Inhibits Factor Xa: Insight Into Its Possible Mechanism of Action" *Blood* 71(2):335–343 (Feb. 1988).
Broze, Jr. et al., "Regulation of Coagulation by a Multivalent Kunitz–Type Inhibitor" *Biochemistry* 29(33):7539–7546 (1990).
Broze, Jr., et al., "Inhibition of Factor VIIa/Tissue Factor by Antithrombin III and Tissue Factor Pathway Inhibitor" *Blood* 82:1679–1680 (1993).
Broze, Jr., George J., "The Role of Tissue Factor Pathway Inhibitor in a Revised Coagulation Cascade" *Sem. in Hematology* 29(3):159–169 (1992).
Carson et al., "The role of tissue factor in the production of thrombin" *Blood. Coag. Fibrinol.* 4:281–292 (1993).
Castro et al., "Does the Kunitz domain from the Alzheimer's amyloid Beta protein precursor inhibit a kallikrein responsible for post–translational processing of nerve growth factor precursor?" *FEBS 08591* 267(2):207–212 (1990).
Chabbat et al., "Aprotinin Is A competitive Inhibitor of The Factor VIIa–Tissue Factor Complex" *Thrombosis Research* 71:205–215 (1993).
Chu et al., "Mosaic structure of globular domains in the human type VI collagen α 3 chain: similarity to von Willebrand Factor, fibronectin, actin, salivary proteins and aprotinin type protease inhibitors" *EMBO Journal* 9(3):385–393 (1990).
Colman, R.W., "The Role of Plasma Proteases In Septic Shock" *The New England J. of Med.* 320(18):1207–1209 (1989).
Creasey et al., "Tissue Factor Pathway Inhibitor Reduces Mortality from *Escherichia coli* Septic Shock" *J. Clin. Invest.* 91:2850–2860 (1993).
Creighton et al., "Biosynthesis, Processing, and Evolution of Bovine Pancreatic Trypsin Inhibitor" *Cold Spring Harbor Symp Quant Biol.* 52:511–519 (1987).
Davie et al., "The Coagulation Cascade: Initiation, Maintenance, and Regulation" *Biochemistry* 30(43):10363–10370 (1991).
Dennis et al., "Kunitz Domain Inhibitors of Tissue Factor—Factor VIIa; I. Potent Inhibitors Selected from Libraries by Phage Display" *Journal of Biological Chemistry* 269(35):22129–22136 (1994).

(List continued on next page.)

*Primary Examiner*—Robert A. Wax
*Assistant Examiner*—Elizabeth Slobodyansky
*Attorney, Agent, or Firm*—Jeffrey S. Kubinec

[57] ABSTRACT

The invention provides compositions having a Factor VIIa active site inhibitor domain and a tissue factor domain for the inhibition of FVIIa. The invention also provides pharmaceutical compositions comprising the novel compositions as well as their use in diagnostic, therapeutic, and prophylactic methods.

4 Claims, 8 Drawing Sheets

OTHER PUBLICATIONS

Dennis et al., "Kunitz Domain Inhibitors of Tissue Factor—Factor VIIa; I. Potent and Specific Inhibitors by Competitive Phage Selection" *Journal of Biological Chemistry* 269(35):22137–22144 (1994).

Drake et al., "Functional Tissue Factor Is Entirely Cell Surface Expressed on Lipopolysaccharide–stimulated Human Blood Monocytes and a Constitutively Tissue Factor–producing Neoplastic Cell Line" *Journal of Cell Biology* 109:389 (1989).

Eigenbrot et al., "Structural effects induced by removal of a disulfide–bridge: the X–ray structure of the C30A/C51A mutant of basic pancreatic trypsin inhibitor at 1.6 Angstrom" *Protein Eng.* 3:591–598 (1990).

Gibbs et al., "Identification of the Factor VIIa Binding Site on Tissue Factor by Homologous Loop Swap and Alanine Scanning Mutagenesis" *Biochemistry* 33:14003–14010 (1994).

Girard et al., "Functional significance of the Kunitz–type inhibitory domains of lipoprotein–associated coagulation inhibitor" *Nature* 338:518–520 (1989).

Girard et al., "Inhibition of Factor VIIa—Tissue Factor Coagulation Activity by a Hybrid Protein" *Science* 248:1421–1424 (1990).

Hagen et al., "Characterization of a cDNA coding for human factor VII" *Proc. Natl. Acad. Sci. USA* 83:2412–2416 (1986).

Hamamoto et al., "Inhibitory Properties of Full–length and Truncated Recombinant Tissue Factor Pathway Inhibitor (TFPI)" *Journal of Biological Chemistry* 268(12):8704–8710 (1993).

Harlos et al., "Crystal structure of the extracellular region of human tissue factor" *Nature* 370:662–666 (1994).

Haskel et al., "Prevention of Arterial Reocclusion After Thrombolysis With Recombinant Lipoprotein–Associated Coagulation Inhibitor" *Circulation* 84:821–827 (1991).

Hochstrasser, "Kunitz–Type Proteinase Inhibitors Derived by Limited Proteolysis of the Inter–α–Trypsin Inhibitor, X" *Biol. Chem. Hoppe–Seyler* 366:473–478 (1985).

Holst et al., "Antithrombotic Properties of a Truncated Recombinant Tissue Factor Pathway Inhibitor in an Experimental Venous Thrombosis Model" *Haemostasis* 23(Suppl. 1):112–117 (1993).

Hynes et al., "X–ray Crystal Structure of the Protease Inhibitor Domain of Alzheimer's Amyloid β–Protein Precursor" *Biochemistry* 29:10018–10022 (1990).

Kelley et al., "Analysis of the Factor VIIa Binding Site on Human Tissue Factor: Effects of Tissue Factor Mutations on the Kinetics and Thermodynamics of Binding" *Biochemistry* 34:10383–10392 (1995).

Kossiakoff et al., "Molecular recognition in biological systems: From activation to inhibition" *Bio. Society Transactions* 21:614–618 (1993).

Kunitz et al., "Isolation from Beef Pancreas of Crystalline Trypsinogen, Trypsin, a Trypsin Inhibitor, and an Inhibitor–Trypsin Compound" *J. Gen. Physiol.* 19:991–1007 (1936).

Kunkel et al., "Rapid and Efficient Site–specific Mutagenesis Without Phenotypic Selection" *Methods in Enzymology* 154:367–382 (1987).

Laskowski et al., "Protein Inhibitors of Proteinases" *Ann. Rev. Biochem.* 49:593–626 (1980).

Lauritzen et al., "BPTI and N–Terminal Extended Analogues Generated by Factor $X_a$ Cleavage and Cathepsin C Trimming of a Fusion Protein Expressed in *Escherichia coli*" *Prot. Express. Purif.* 2:372–378 (1991).

Lawson et al., "Complex–dependent Inhibition of Factor VIIa by Antithrombin III and Heparin" *Journal of Biological Chemistry* 268(2):767–770 (1993).

Mann, Kenneth G., "Correspondence—Response" *Blood* 82:1680–1681 (1993).

Maraganore, "Thrombin, Thrombin Inhibitors, and the Arterial Thrombotic Process" *Thrombosis and Haemostasis* 70(1):208–211 (1993).

Maraganore et al., "Design and Characterization of Hirulogs: A Novel Class of Divalent Peptide Inhibitors of Thrombin" *Biochemistry* 29:7095–7101 (1990).

Means et al., "Chemical Modifications of Proteins: History and Applications" *Bioconjugate Chemistry* 1:2–12 (1990).

Morrissey et al., "Molecular Cloning of cDNA for Tissue Factor, the Cellular Receptor for the Initiation of the Coagulation Protease Cascade" *Cell* 50(1):129–135 (1987).

Muller et al., "Structure of the Extracellular Domain of Human Tissue Factor: Location of the Factor VIIa Binding Site" *Biochemistry* 33:10864–10870 (1994).

O'Brien et al., "Factor VIII–Bypassing Activity of Bovine Tissue Factor Using the Canine Hemophilic Model" *J. Clin. Invest.* 82:206–211 (1988).

Paborsky et al., "Mammalian Cell Transient Expression of Tissue Factor for the Production of Antigen" *Protein Eng.* 3(6):547–553 (1990).

Paborsky et al., "Purification of Recombinant Human Tissue Factor" *Biochemistry* 28(20):8072–8077 (1989).

Pawashe et al., "A Monoclonal Antibody Against Rabbit Tissue Factor Inhibits Thrombus Formation in Stenotic Injured Rabbit Carotid Arteries" *Circ. Res.* 74:56–63 (1994).

Petersen et al., "Characterization of Human Tissue Factor Pathway Inhibitor Variants Expressed in *Saccharomyces cerevisiae*" *Journal of Biological Chemistry* 268:13344–13351 (1993).

Rao et al., "Binding of Factor VIIa to Tissue Factor Permits Rapid Antithrombin III/Heparin Inhibition of Factor VIIa" *Blood* 81(10):2600–2607 (1993).

Rao et al., "Tissue Factor Residues $Lys^{165}$ and $Lys^{166}$ Are Essential for Rapid Formation of the Quaternary Complex of Tissue Factor–VIIa with Xa–Tissue Factor Pathway Inhibitor" *Biochemistry* 34:10867–10871 (1995).

Rapaport et al., "Initiation and Regulation of Tissue Factor–Dependent Blood Coagulation" *Aterioscler. Thromb.* 12:1111–1121 (1992).

Roberts et al., "Directed evolution of a protein: Selection of potent neutrophil elastase inhibitors displayed on M13 fusion phage" *Proc. Natl. Acad. Sci USA* 89:2429–2433 (1992).

Roy et al., "Lysine Residues 165 and 166 Are Essential for the Cofactor Function of Tissue Factor" *Journal of Biological Chemistry* 266:22063 (1991).

Roy et al., "Self–association of Tissue Factor as Revealed by Chemical Cross–linking" *Journal of Biological Chemistry* 266(8):4665–4668 (1991).

Ruf et al., "Cofactor Residues Lysine 165 and 166 Are Critical for Protein Substrate Recognition by the Tissue Factor—Factor VIIa Protease Complex" *Journal of Biological Chemistry* 267:6375 (1992).

Ruf et al., "Mutational Mapping of Functional Residues in Tissue Factor: Identification of Factor VII Recognition Determinants in Both Structural Modules of the Predicted Cytokine Receptor Homology Domain" *Biochemistry* 33:1565–1572 (1994).

Ruf et al., "Tissue Factor Residues 157–167 Are Required for Efficient Proteolytic Activation of Factor X and Factor VII" *Journal of Biological Chemistry* 267:22206–22210 (1992).

Ruhlmann et al., "Structure of the Complex formed by Bovine Trypsin and Bovine Pancreatic Trypsin Inhibitor" *J. Mol. Biol.* 77:417 436 (1973).

Schecter et al., "On the Size of the Active Site in Proteases. I. Papain" *Biochem. & Biophys. Res. Comm.* 27:157–162 (1967).

Schullck et al., "Key Ligand Interface Residues in Tissue Factor Contribute Independently to Factor VIIa Binding" *Journal of Biological Chemistry* 269:19399–19403 (1994).

Scott et al., "Kinetics of Inhibition of Human Plasma Kallikrein by a Site–Specific Modified Inhibitor $Arg^{15}$–Aprotinin: Evaluation Using a Microplate System and Comparison With Other Proteases" *Blood* 69(5):1431–1436 (1987).

Sinha et al., "Conversion of the Alzheimer's β–Amyloid Precursor Protein (APP) Kunitz Domain into a Potent Human Neutrophil Elastase Inhibitor" *Journal of Biological Chemistry* 266(31):21011–21013 (1991).

Taubman et al., "Agonist–mediated Tissue Factor Expression in Cultured Vascular Smooth Muscle Cells" *J. Clin. Invest.* 91:547–552 (Feb. 1993).

Taylor, FB Jr et al., "Lethal *E. coli* septic shock is prevented by blocking tissue factor with monoclonal antibody" *Circ. Shock* 33(3):127–134 (Mar. 1991).

Thim et al., "Amino Acid Sequence and Postranslational Modifications of Human Factor $VII_a$ from Plasma and Transfected Baby Hamster Kidney Cells" *Biochemistry* 27:7785–7793 (1988).

Van Den Besselaar et al., "Tissue Factor–Induced Coagulation Can Be Inhibited by Aprotinin (Trasylol)" *Thrombosis and Haemostasis* 69:298–299 (1993).

Vedvick et al., "High–level secretion of biologically active aprotinin from the yeast *Pichia pastoris*" *J. Indust. Microbiol.* 7:197–201 (1991).

Vetr et al., "The domain structure of the inhibitor subunit of human inter–α–trypsin inhibitor reflects the exon structure of its gene" *FEBS 06902 Letter* 245 (1,2):137–140 (1989).

Wagner et al., "High Level Expression, Purification, and Characterization of The Kunitz–Type Protease Inhibitor Domain of Protease Nexin–2/Amyloid Beta–Protein Precursor" *Biochem. & Biophys. Res. Comm.* 186:1138–1145 (1992).

Warr et al., "Disseminated Intravascular Coagulation in Rabbits Induced by Administration of Endotoxin or Tissue Factor: Effect of Anti–Tissue Factor Antibodies and Measurement of Plasma Extrinsic Pathway Inhibitor Activity" *Blood* 75:1481 (1990).

Wells et al., "Cassette Mutagenesis: an Efficient Method for Generation of Multiple Mutations at Defined Sites" *Gene* 34(2–3):315–323 (1985).

Wilcox et al., "Localization of Tissue Factor in the Normal Vessel Wall and in the Atherosclerotic Plaque" *Proc. Natl. Acad. Sci. USA* 86:2839–2843 (1989).

Williams et al., "The Kinetics of Reversible Tight–Binding Inhibition" *Methods Enzymol.* 63:437–467 (1979).

Williams et al., "Peptide Chloromethyl Ketones as Labeling Reagents" *Methods in Enzymology* 222:503–513 (1993).

Williams et al., "Zymogen/Enzyme Discrimination Using Peptide Chloromethyl Ketones" *Journal of Biological Chemistry* 264:7536–7540 (1989).

FACTOR VIIA INHIBITORS

This is a divisional application of U.S. Ser. No. 08/566,800, filed Dec. 4, 1995 abandoned.

BACKGROUND OF THE INVENTION

FIELD OF THE INVENTION

This invention relates to novel compositions which bind to and inhibit an activity associated with plasma Factor VII/Factor VIIa. Specifically, the invention provides molecules having a Factor VIIa active site inhibitor domain and a tissue factor domain. According to a preferred aspect, the two domains of the hybrid molecule of the present invention are linked via flexible peptide linker domain. The invention also relates to pharmaceutical compositions comprising the novel compositions as well as their use in diagnostic, therapeutic, and prophylactic methods.

DESCRIPTION OF RELATED DISCLOSURES

Factor VIIa (FVIIa) is a two-chain, 50 kilodalton (kDa), vitamin K-dependent, plasma serine protease which participates in the complex regulation of in vivo hemostasis. Factor VIIa is generated by proteolysis of a single peptide bond from its single chain zymogen, Factor VII, which is present at approximately 0.5 µg/ml in plasma. The conversion of zymogen Factor VII into the activated two-chain molecule occurs by cleavage of an internal peptide bond. In human Factor VII, the cleavage site is at Arg152-Ile153 (Hagen et al., (1986) Proc. Natl. Acad. Sci. U.S.A. 83:2412–2416; Thim et al., (1988) Biochem. 27:7785–7793,). In the presence of calcium ions, Factor VIIa binds with high affinity to tissue factor (TF), an integral membrane protein. TF is a cofactor for Factor VIIa, enhancing the proteolytic activation of its substrates Factors VII (FVII), Factor IX (FIX) and Factor X (FX).

TF is a 263 amino acid residue glycoprotein composed of a 219 residue extracellular domain, a single transmembrane domain, and a short cytoplasmic domain (Morrissey, J. H., et al., (1987) 50:129). The TF extracellular domain is composed of two fibronectin type III domains of about 105 amino acids each. The binding of FVIIa is mediated entirely by the TF extracellular domain (Muller et al., (1994) Biochem. 33:10864–10870; Gibbs et al., (1994) Biochem. 33:14003–14010; Ruf et al., (1994) Biochem. 33:1565–1572). The structure of the TF extracellular domain has recently been determined by x-ray crystallography (Harlos et al., (1994) Nature 370:662–666; Muller et al., (1994) Biochemistry 33:10864).

The TF extracellular domain has also has been extensively characterized by alanine scanning mutagenesis (Kelley et al., (1995) Biochemistry, 34:10383–10392; Gibbs et al., (1994) supra; Ruf et al., (1994) supra). Residues in the area of amino acids 16–26 and 129–147 contribute to the binding of FVIIa as well as the coagulant function of the molecule. Residues Lys20, Trp45, Asp58, Tyr94, and Phe140 make a large contribution (1 kcal/mol) to the free energy (ΔG) of binding to FVIIa (Kelley et al., (1995) supra).

Residues in the area of amino acids 157–168 contribute to the procoagulant function of TF-FVIIa (Kelley et al., (1995) supra; Ruf et al., (1992) J. Biol. Chem. 267:22206–22210) but are not important for FVII/FVIIa binding. It has been shown that lysine residues 165 and 166 are important to TF cofactor function but do not participate in FVIIa complex formation (Roy et al., (1991) J. Biol. Chem. 266:22063; Ruf et al., (1992) J. Biol. Chem. 267:6375). Alanine substitution of these lysine residues results in a decreased rate of FX activation catalyzed by the TF-FVIIa complex (Ruf et al., (1992) supra). Lysine residues 165 and 166 are located on the C-terminal fibronectin type III domain of TF on the opposite surface of the molecule from residues found to be important for FVIIa binding on the basis of mutagenesis results (Kelley et al., (1995) supra). A set of residues, Trp158, Lys159, Ser163, Gly164, Lys165, Lys166, and Tyr185 play a role in the coagulant function of soluble TF but do not participate in FVIIa binding (Kelley et al., (1995) supra).

TF is expressed constitutively on cells separated from plasma by the vascular endothelium (Carson, S. D. and J. P. Brozna, (1993) Blood Coag. Fibrinol. 4:281–292). Its expression on endothelial cells and monocytes is induced by exposure to inflammatory cytokines or bacterial lipopolysaccharides (Drake et al., (1989) J. Cell Biol. 109:389). Upon tissue injury, the exposed extracellular domain of TF forms a high affinity, calcium dependent complex with FVII. Once bound to TF, FVII can be activated by peptide bond cleavage to yield serine protease FVIIa. The enzyme that catalyzes this step in vivo has not been elucidated, but in vitro FXa, thrombin, TF-FVIIa and FIXa can catalyze this cleavage (Davie, et al., (1991) 30:10363–10370). FVIIa has only weak activity upon its physiological substrates FX and FIX whereas the TF-FVIIa complex rapidly activates FX and FIX.

The TF-FVIIa complex constitutes the primary initiator of the extrinsic pathway of blood coagulation (Carson, S. D. and Brozna, J. P., (1993) Blood Coag. Fibrinol. 4:281–292; Davie, E. W. et al., (1991) Biochemistry 30:10363–10370; Rapaport, S. I. and L. V. M. Rao, (1992) Arterioscler. Thromb. 12:1111–1121). The complex initiates the extrinsic pathway by activation of FX to Factor Xa (FXa), FIX to Factor IXa (FIXa), and additional FVII to FVIIa. The action of TF-FVIIa leads ultimately to the conversion of prothrombin to thrombin, which carries out many biological functions (Badimon, L. et al., (1991) Trends Cardiovasc. Med. 1:261–267). Among the most important functions of thrombin is the conversion of fibrinogen to fibrin, which polymerizes to form a clot. The TF-FVIIa complex also participates as a secondary factor in extending the physiological effects of the contact activation system.

The involvement of this plasma protease system has been suggested to play a significant role in a variety of clinical manifestations including arterial and venous thrombosis, septic shock, adult respiratory distress syndrome (ARDS), disseminated intravascular coagulation (DIC) and various other disease states (Haskel, E. J. et al., (1991) Circulation 84:821–827); Holst, J. et al., (1993) Haemostasis 23 (suppl. 1):112–117; Creasey, A. A. et al., (1993) J. Clin. Invest. 91:2850–2860; see also, Colman R. W. (1989) N. Engl. J. Med 320:1207–1209; Bone, R. C. (1992) Arch. Intern. Med. 152:1381–1389). Overexpression and/or aberrant utilization of TF has been linked to the pathophysiology of both thrombosis and sepsis (Taylor et al., (1991) Circ. Shock 33:127; Warr et al., (1990), Blood 75:1481; Pawashe et al., (1994) Circ. Res. 74:56). TF is expressed on cells found in the atherosclerotic plaque (Wilcox et al., (1989) Proc. Natl. Acad. Sci. U.S.A. 86:2839). Additionally, TF has been implicated in tumor metastasis (Bromberg et al., (1995) Proc. Natl. Acad. Sci., U.S.A., 92:8205).

The presence in serum of an endogenous inhibitor of TF-FVIIa has long been recognized (Schneider, C. L., (1946) Am. J. Physiol. 149:123). Following initiation of the coagulation cascade, TF-FVIIa is regulated by tissue factor pathway inhibitor (TFPI), a feedback inhibitor that prevents further activation of zymogen substrates (Broze Jr., G. J. et al., (1990) Biochemistry 29:7539–7546; Broze Jr., G. J., (1992) Semin. Hematol. 29:159–169). TFPI is also known as LACI or EPI for lipoprotein associated coagulation inhibitor and extrinsic pathway inhibitor, respectively. TFPI contains an acidic amino terminal region followed by three Kunitz-type domains and a basic carboxyl terminal region. TFPI is thought to inhibit TF-FVIIa in a FXa dependent manner, first binding FXa via the second Kunitz domain followed by binding FVIIa via the first Kunitz domain (Girard, T. J. (1989) et al., Nature 338:518–520). In the absence of FXa, TFPI is a poor inhibitor of the TF-FVIIa complex (Girard, T. J. (1990) et al., Science 248:1421–1424).

Variants of TFPI have been made that also inhibit TF-FVIIa activity. A variant that contains the first two Kunitz domains (residues 1–161) has been made and characterized (Hamamoto et al. (1993) J. Biol. Chem. 268:8704–8710; Petersen et al. (1993) J. Biol. Chem. 268:13344–13351). International Publication No. WO 91/02753 as well as U.S. Pat. No. 5,312,736 describe TFPI variants that retain their serine protease inhibitory activity but have a decreased binding affinity for heparin. A TFPI-FXa hybrid protein is able to inhibit TF-FVIIa induced coagulation of normal plasma in an in vitro coagulation assay with a greater activity than TFPI alone (Girard et al., (1990) Nature 248:1421–1424).

TFPI and variants have been shown to affect hemostasis in animal models of arterial reocclusion after thrombolysis (Haskel, E. J. et al., (1991) Circulation 84:821–827), venous thrombosis (Holst, J. et al., (1993) Haemostasis 23 (suppl. 1):112–117), and disseminated intravascular coagulation resulting from septic shock (Creasey, A. A. et al., (1993) J. Clin. Invest. 91:2850–2860). However, TFPI may not have all of the properties desired for an anticoagulant agent for the treatment of thrombotic disease.

Recently, the serpin antithrombin III (ATIII) has also been shown to inhibit TF-FVIIa activity in the presence of heparin (Rao, L. V. M. et al., (1993) Blood 81:2600–2607; Lawson, J. H. (1993) et al., J. Biol. Chem. 268:767–770; Broze Jr., G. J. et al., (1993) Blood 82:1679–1680; Mann, K. G., (1993) Blood 82:1680–1681). Inhibition of TF-FVIIa by TFPI is reversible, whereas inhibition by ATIII is essentially irreversible. The relative importance of ATIII/heparin inhibition of TF-FVIIa versus TFPI in vivo is unknown.

Bovine pancreatic trypsin inhibitor (BPTI), also referred to as aprotinin, has recently been shown to competitively inhibit TF-FVIIa activity, albeit with relatively weak affinity ($K_i=30$ $\mu$M) (Chabbat, J. et al., (1993) Thromb Res 71:205–215). In addition, BPTI has recently been shown to inhibit TF-induced coagulation; however, ca. 75 $\mu$M was needed to prolong the clotting time 1.4-fold in a PT assay (van den Besselaar, A. M. H. P. et al., (1993) Thromb. Haemostas. 69:298–299).

Recently, the Kunitz domain of Alzheimer's amyloid β-protein precursor (APPI), which is structurally similar to BPTI (Hynes, T., et al., (1990) Biochemistry 29:10018–10022), was used as a scaffold for phage display of a large library of variants to select potent and specific active site inhibitors of tissue factor-Factor VIIa (Dennis, M. S., and Lazarus, R. A., (1994) J. Biol. Chem. 269:22129–22136; Dennis, M. S., and Lazarus, R. A., (1994)J. Biol. Chem. 269:22137–22144). International Publication No. WO 95/23860 describes the generation of Kunitz-type inhibitors of Factor VIIa.

The foregoing FVIIa inhibitors have been classified as Kunitz-type serine protease inhibitors (TFPI, BPTI, APPI, for example). Kunitz-type serine protease inhibitors are a well characterized family of proteins that exhibit extensive structural homology including a characteristic tertiary fold containing an extended binding loop that fits into the active site of the cognate serine protease (Bode, W., and Huber, R., (1992) Eur. J. Biochem. 204:433–451). Kunitz-type serine protease inhibitors are known to be slow, tight-binding, reversible inhibitors of serine proteases such as FVIIa that bind to the active-site and inhibit according to the standard mechanism (Laskowski, Jr., M. and Kato, I., (1980) Ann. Rev. Biochem. 49:593–626).

In a Kunitz-type domain/serine protease complex, the side chain of residue 15 of the Kunitz-type domain fills the $P_1$ position preceding the scissile peptide bond. The $P_1$ residue refers to the position preceding the scissile peptide bond of the substrate or inhibitor and fits into the $S_1$ binding site as defined by Schecter and Berger (1967) Biochem. Biophys. Res. Commun., 27:157–162. Cleavage between the $P_1$ and $P_1'$ residues occurs very slowly if at all (Bode, W. and Huber, R., (1992) Eur. J. Biochem. 204:433–451; Laskowski, M., Jr. and Kato, I., (1980) Annu. Rev. Biochem. 49:593–626).

Of the many interactions between the serine protease subsites and the side chains in the primary binding loop of Kunitz-type domain serine protease inhibitors ($P_5$-$P_4'$) (Bode, W. and Huber, R., (1992) Eur. J. Biochem. 204:433–451; Laskowski, M., Jr. and Kato, I., (1980) Annu. Rev. Biochem. 49:593–626), the interactions of the $P_1$ residue with the specificity pocket are energetically most important and therefore represent the primary specificity determinants. Although the amino acid at the $P_1$ position generally dominates the affinity of inhibitors for the serine protease active site (Scott, C. F. et al., (1987) Blood 69:1431–1436; Laskowski, M., Jr. and Kato, I., (1980) supra; Beckmann, J. et al., (1988) Eur. J. Biochem. 176:675–682; Sinha, S. et al., (1991) J. Biol. Chem. 266:21011–21013), residues outside this region (11–14 and 16–19 as well as residue 34 of secondary binding loop) are also known to play a role in binding affinity and specificity towards serine proteases (Kossiakoff, A. A. et al., (1993) Biochem. Soc. Trans. 21:614–618); Roberts, B. L. et al., (1992) Proc Natl Acad Sci U.S.A. 89: 2429–2433). The crystal structures of Kunitz-type domains reveal residues within the primary binding loop that are likely to make contact with the serine protease (Hynes, T. R. et al., (1990) supra; Bode, W. and Huber, R., (1992) supra; Kossiakoff, A. A. (1993), supra).

Antagonists to tissue factor have also been demonstrated. Neutralizing anti-TF monoclonal antibodies have been shown to prevent death in a baboon model of sepsis (Taylor et al., (1991) Circ. Shock 33:127), attenuate endotoxin-induced DIC in rabbits (Warr et al., (1990), Blood 75:1481), and to prevent thrombus reformation in a rabbit model of arterial thrombosis (Pawashe et al., (1994) Circ. Res. 74:56). Incorporation of lysine to alanine mutations at amino acid residues 165 and 166 of soluble tissue factor results in a molecule that binds FVIIa with an affinity comparable to wild type soluble tissue factor (Kelley et al., (1995) supra). TF residues Lys 165 and Lys 166 have been shown to be important for inhibition of TF-FVIIa by the TFPI-FXa complex (Rao and Ruf, (1995) Biochemistry 34:10867–10871). The rate of inhibition by TFPI-FXa is decreased for FVIIa in complex with a TF mutant containing Lys to Ala substitutions at positions 165 and 166 as compared to FVIIa in complex with wild-type TF. Variants of tissue factor have also been produced that bind to functional FVIIa but which have decreased procoagulant activity (International Publication No WO 94/28017). These molecules inactivate the cofactor activity of tissue factor in the TF-FVIIa complex but do not alter the ability of the molecule to complex FVIIa.

SUMMARY OF THE INVENTION

The present invention provides compositions which inhibit a TF-FVIIa mediated or associated process such as the catalytic conversion of FVII to FVIIa, FIX to FIXa, or FX to FXa and thereby block initial events of the extrinsic pathway of blood coagulation. In addition, the compositions of the present invention are capable of neutralizing the thrombotic effects of endogenous tissue factor by competing with endogenous tissue factor for binding to FVII or FVIIa. Advantageously, the compositions allow for a potent inhibition of the TF-FVIIa complex providing, in preferred embodiments, for low dose pharmaceutical formulations. The compositions of the present invention are useful in therapeutic and prophylactic methods for inhibiting TF-FVIIa mediated or associated processes.

The compositions of the present invention comprise a FVIIa active site inhibitor domain and a TF domain. According to a preferred aspect of the present invention, the TF domain competes with endogenous TF for binding to FVII/FVIIa but has a decreased ability to act as a cofactor for the conversion of FVII to FVIIa, FIX to FIXa or FX to FXa. The FVIIa active site inhibitor domain of the compositions of the present invention binds to the serine protease active site of FVIIa and prevents catalytic activation of its zymogen substrates. In a preferred embodiment the active site inhibitor domain of the composition of the present invention is a reversible active site serine protease inhibitor molecule.

According to certain preferred aspects of the present invention the compositions further comprise a linker domain located between the FVIIa active site inhibitor domain and the TF domain. The linker domain is preferably a hydrophilic flexible domain comprising a -(Gly)$_4$-Ser- linker module.

In one embodiment, the composition of the present invention is a polypeptide and the invention encompasses a composition of matter comprising an isolated nucleic acid, preferably DNA, encoding the polypeptide of the invention. According to this aspect, the invention further comprises an expression control sequence operably linked to the DNA molecule, an expression vector, preferably a plasmid, comprising the DNA molecule, where the control sequence is recognized by a host cell transformed with the vector, and a host cell transformed with the vector.

The composition of the present invention may be made by a process which includes the steps of isolating or synthesizing nucleic acid sequences encoding any of the amino acid sequences of the invention, ligating the nucleic acid sequence into a suitable expression vector capable of expressing the nucleic acid sequence in a suitable host, transforming the host with the expression vector into which the nucleic acid sequence has been ligated, and culturing the host under conditions suitable for expression of the nucleic acid sequence, whereby the protein encoded by the selected nucleic acid sequence is expressed by the host. Preferably, the polypeptide is then recovered from the host cell culture. In this process, the ligating step may further contemplate ligating the nucleic acid into a suitable expression vector such that the nucleic acid is operably linked to a suitable secretory signal, whereby the amino acid sequence is secreted by the host. The secretory signal may be selected from the group consisting of the leader sequence, for example, of stII, lamB, herpes gD, lpp, alkaline phosphatase, invertase, and alpha factor and is preferably stII.

The present invention further extends to therapeutic applications for the compositions described herein. Thus the invention includes a pharmaceutical composition comprising a pharmaceutically acceptable excipient and the composition of the invention. Pharmaceutical compositions comprising these molecules can be used in the treatment or prophylaxis of thrombotic or coagulopathic related diseases or disorders including vascular diseases and inflammatory responses. These applications include, for example, a method of treating a mammal for which inhibiting TF-FVIIa is indicated comprising administering a pharmaceutically effective amount of the pharmaceutical composition to the mammal. Such indications include; deep venous thrombosis, arterial thrombosis, post surgical thrombosis, coronary artery bypass graft (CABG), percutaneous transdermal coronary angioplasty (PTCA), stroke, tumor metastasis, inflammation, septic shock, hypotension, ARDS, and DIC. The compositions of the present invention may also be used as an adjunct in thrombolytic therapy.

DETAILED DESCRIPTION OF THE PREFERRED EMBODIMENTS

Definitions

Abbreviations used throughout the description include: FIXa for Factor IXa; FXIa for Factor XIa; FXa for Factor Xa; TF for tissue factor; FVII for zymogen factor VII; FVIIa for Factor VIIa; TF-FVIIa for tissue factor-Factor VIIa complex; FVII/FVIIa for FVII and/or FVIIa; BPTI for basic pancreatic trypsin inhibitor; APPI for the Kunitz protease inhibitor domain of Alzheimer's amyloid β-protein precursor inhibitor (Hynes et al., (1990) supra); -(Gly)$_4$-Ser-, and G$_4$S for a 5 amino acid polypeptide having the amino acid sequence Gly-Gly-Gly-Gly-Ser SEQ ID NO. 58; TFPI for tissue factor pathway inhibitor; $K_i^*$ for apparent equilibrium dissociation constant; PT for prothrombin time; APTT for activated partial thromboplastin time.

Figure 1:
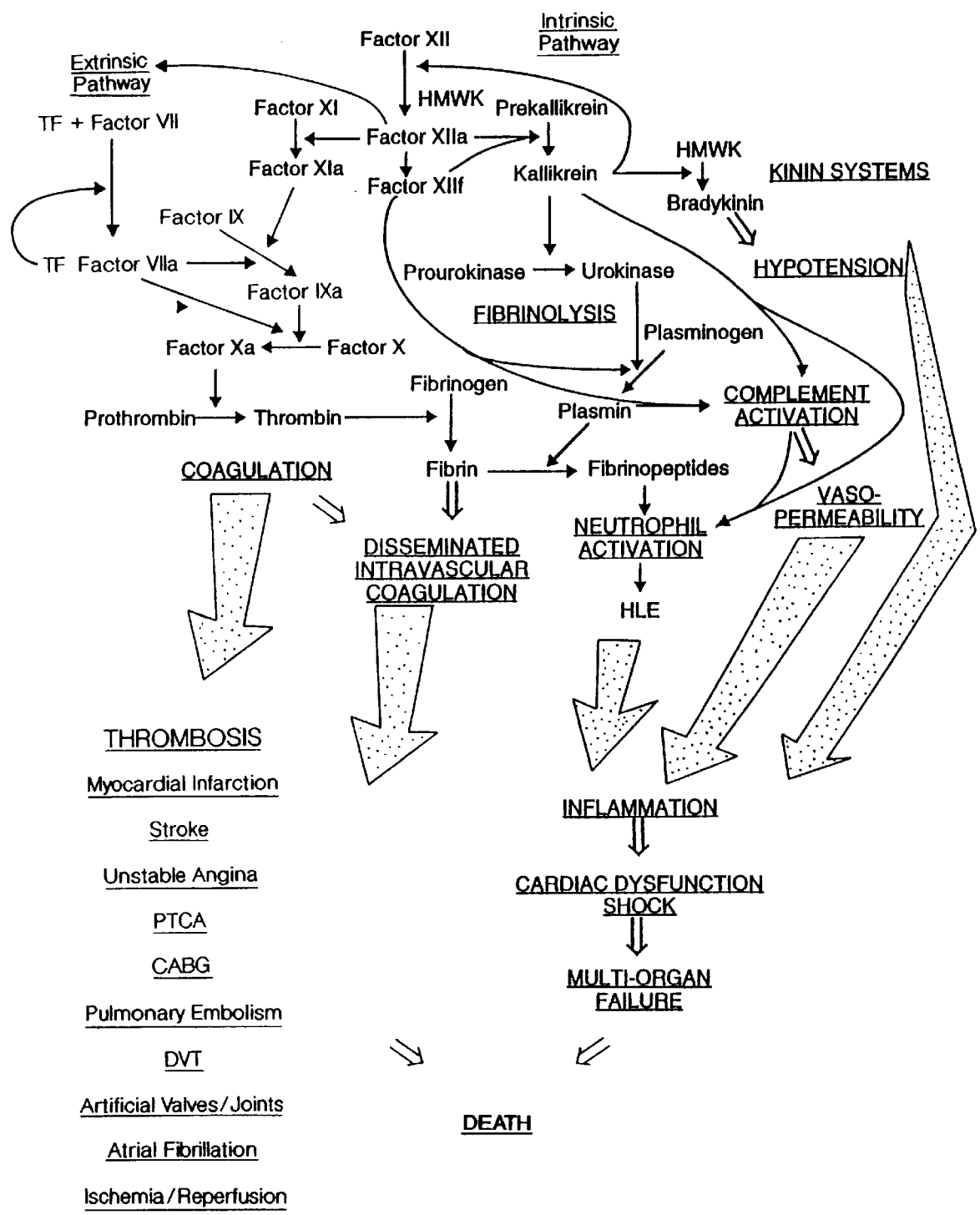
FIG. 1 depicts a schematic outline of selected enzymes and mediators that modulate the coagulation, contact, fibrinolytic, inflammatory, and complement pathways. Activation of these pathways can lead to the clinical states indicated.
Figure 2:
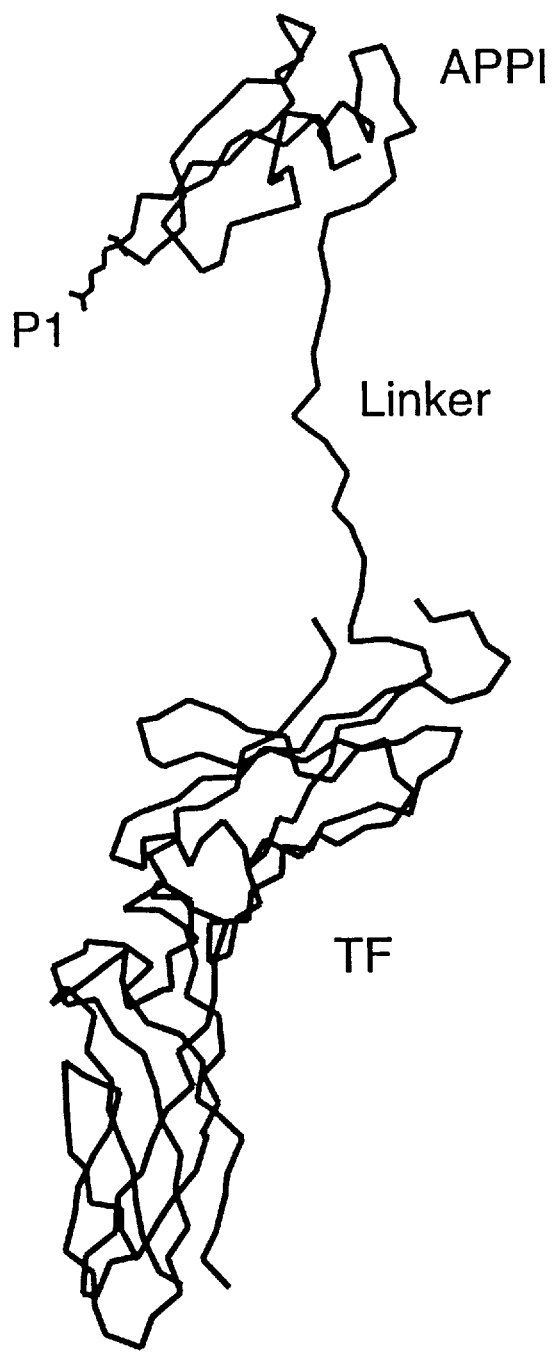
FIG. 2 depicts a model of an exemplary composition. The composition comprises a fusion protein having a TF domain, an active site inhibitor domain (APPI), and a linker domain. The structure of TF determined at 2.4 Å resolution (Muller et al., (1994) supra) was used for the TF portion of the molecule. The Kunitz-type domain is based upon the structure determined for APPI (Hynes et al., (1990) supra). A 22 residue polypeptide linker was modeled in extended conformation to connect the C-Terminus of the Kunitz-domain to the N-terminus of TF. The distance between these termini is about 60 Å. The C-terminus of TF is at the bottom of the molecule.

A TF-FVIIa mediated or associated process or event, or equivalently, an activity associated with plasma FVIIa, according to the present invention is any event which requires the presence of TF-FVIIa. The general mechanism of blood clot formation is reviewed by Ganong, in Review of Medical Physiology, 13th ed., Lange, Lost Altos Calif., pp411–414 (1987). Coagulation requires the confluence of two processes, the production of thrombin which induces platelet aggregation and the formation of fibrin which renders the platelet plug stable. As outlined in FIG. 1, the process comprises several stages each requiring the presence of discrete proenzymes and procofactors. The process ends in fibrin crosslinking and thrombus formation. Fibrinogen is converted to fibrin by the action of thrombin. Thrombin, in turn, is formed by the proteolytic cleavage of prothrombin. This proteolysis is effected by FXa which binds to the surface of activated platelets and in the presence of FVa and calcium, cleaves prothrombin. TF-FVIIa is required for the proteolytic activation of FX by the extrinsic pathway of coagulation. Therefore, a process mediated by or associated with TF-FVIIa, or an activity associated with FVIIa includes any step in the coagulation cascade from the formation of the TF-FVII complex to the formation of a fibrin platelet clot and which initially requires the presence TF-FVIIa.

For example, the TF-FVIIa complex initiates the extrinsic pathway by activation of FX to FXa, FIX to FIXa, and additional FVII to FVIIa. TF-FVIIa mediated or associated process, or FVIIa activity, can be conveniently measured employing standard assays such as those described in Roy, S., (1991) J. Biol. Chem. 266:4665–4668, and O'Brien, D., et al., (1988) J. Clin. Invest. 82:206–212 for the conversion of Factor X to Factor Xa in the presence of Factor VII and other necessary reagents.

A TF-FVIIa related disease or disorder is meant to include chronic thromboembolic diseases or disorders associated with fibrin formation including vascular disorders such as deep venous thrombosis, arterial thrombosis, stroke, tumor metastasis, thrombolysis, arteriosclerosis and restenosis following angioplasty, acute and chronic indications such as inflammation, septic shock, septicemia, hypotension, adult respiratory distress syndrome (ARDS), disseminated intravascular coagulapathy (DIC) and other diseases. The TF-FVIIa related disorder is not limited to in vivo coagulopathic disorders such as those named above but includes ex vivo TF-FVIIa related processes such as coagulation that may result from the extracorporeal circulation of blood, including blood removed in-line from a patient in such processes as dialysis procedures, blood filtration, or blood bypass during surgery.

The terms "tissue factor protein" and "wild type tissue factor" are used to refer to a polypeptide having an amino acid sequence corresponding to a naturally occurring mammalian tissue factor or a recombinant tissue factor having an amino acid sequence of a naturally occurring tissue factor which is capable of inducing blood coagulation through its interaction with plasma FVII/FVIIa. Naturally occurring TF includes human species as well as other animal species such as rabbit, rat, porcine, non human primate, equine, murine, and ovine tissue factor. The amino acid sequence of the mammalian tissue factor proteins are generally known or obtainable through conventional techniques. The human sequence as well as the number given to the amino acids are those described by Morrissey, J. H., et al., (1987) 50:129.

"hTFAA" and "K165A:K166AsTF" refer to a soluble tissue factor protein variant having the amino acid sequence of human TF as described above from amino acid 1 to amino acid 219 and wherein the naturally occurring Lys amino acids at positions 165 and 166 are replaced with Ala residues.

By "substitution" of any amino acid is meant that an amino acid of the wild-type tissue factor has been replaced by chemical or enzymatic or other appropriate means with a moiety other than a wild-type amino acid.

The terms "Kunitz-type serine protease inhibitor domain," "Kunitz-type domain," "Kunitz domain," "KD" and the like are used interchangeably herein to refer to an approximately 58 amino acid residue polypeptide characterized by a conservation of cysteine residues with the serine protease inhibitor BPTI (bovine pancreatic trypsin inhibitor; Creighton and Charles, (1987) Cold Spring Harbor Symp. Quant. Biol. 52:511–519) first isolated in crystalline form in 1936 (Kunitz, M., and Northop, J. H., (1936) J. Gen.

Physiol. 19:991–1007). Kunitz domains share cysteine residue placement, tertiary folding, and structural characteristics. A family of proteins has been identified containing one, two or three Kunitz domains. The family includes; LACI (lipoprotein-associated coagulation inhibitor, also TFPI; Broze, Jr. G. J., et al., (1990) Biochemistry 29:7539–7546); APPI (Alzheimer's amyloid β-protein precursor; Hynes, T. R., (1990) Biochemistry 29:10018–10022); the α-3 chain of human type VI collagen (see WO 93/14119) and inter-α-trypsin inhibitor (Hochstrasser, K. E., (1985) Biol. Chem. Hoppe-Seyler 366:473).

Kunitz domains contain six specifically spaced cysteines that are present naturally in disulfide bonds (Bode, W., and Huber, R., (1992) Eur. J. Biochem. 204:433–451). The three disulfide bridges stabilize the protein and are partially responsible for the overall 3-dimensional folding characteristic of a Kunitz domain. In the 58 residue Kunitz type serine protease BPTI and APPI, cysteines are present at residues 5, 14, 30, 38, 51, and 55. The removal of a one disulfide bridge, however is not accompanied by a large structural change (Eigenbrot, C., et al., (1990) Protein Eng. 3:591–598.

The crystal structure of Kunitz domain type serine protease inhibitors has been determined for BPTI and APPI (Hynes, T. R., et al., (1990) Biochem., 29:10018–10022). A central anti-parallel three-stranded β-sheet and a C-terminal α-helix form the core of the domain (Bode, W., and Huber, R., supra). The segments of the core domain form the supporting scaffold for the exposed primary binding loop of the properly folded protein (the "primary binding loop" as defined herein)(Bode, W., and Huber, R., supra). A secondary binding loop participates along with the primary binding loop to define the interface between the Kunitz domain and the cognate protease target (Rühlman, A., et al., (1973) J. Mol. Biol. 77:417–436).

The "primary binding loop" of a Kunitz domain is designated by $P_5-P_4-P_3-P_2-P_1-P_1'-P_2'-P_3'-P_4'$ (residues 11–19 APPI). The term "$P_1$" is used herein to refer to the position preceding the scissile peptide bond of the serine protease inhibitors as previously defined Similarly, the term "$P_1'$" is used to refer to the position following the scissile peptide bond of the inhibitor. Increasing numbers refer to the next consecutive position preceding (e.g., $P_2$ and $P_3$) and following (e.g., $P_2'$ and $P_3'$) the scissile bond. The residue numbering corresponds to that of BPTI such that residue 15 is at the $P_1$ position.

The term "active site" and the like when used herein with reference to FVIIa refer to the catalytic and zymogen substrate binding site, including the "$S_1$" site of FVIIa as that term is defined by Schecter, I., and Berger, A., (1967) Biochem. Biophys. Res. Commun. 27:157–162

The term "amino acid" within the scope of the present invention is meant to refer to naturally occurring L alpha amino acids or residues. The commonly used one and three letter abbreviations for amino acids are used herein (Lehninger, A. L., Biochemistry, 2d ed., pp. 71–92, (1975), Worth Publishers, New York).

Modes for Carrying out the Invention

The hybrid molecules of the present invention comprise at least two distinct domains. Each molecule of the present invention contains a Factor VIIa active site inhibitor domain which binds to the active site of FVII/FVIIa and a tissue factor domain which binds to FVII/FVIIa through protein-protein interactions at the cofactor binding site. According to the present invention the active site inhibitor domain is linked to the N-terminus of the tissue factor domain, preferably via a flexible amino acid linker domain.

1. Tissue Factor Domain

The tissue factor domain of the compositions of the present invention is a tissue factor protein variant which by virtue of, for example, an amino acid substitution, insertion, or deletion in the amino acid sequence of a mammalian tissue factor protein, or by virtue of glycosylation variation including deglycosylated or unglycosylated tissue factor molecules, is capable of neutralizing the ability of tissue factor to induce blood coagulation while retaining at least its ability to bind to Factor VII/VIIa. In a particular embodiment, the TF domain in complex with FVIIa has a decreased ability to catalyze the conversion of substrate Factor X to Factor Xa product. Thus, the tissue factor domain of the present invention is believed to, without limitation, compete with wild-type tissue factor for the cofactor binding site of Factor VII/VIIa, thereby neutralizing or preventing wild type tissue factor from acting as a cofactor in the coagulation cascade.

The tissue factor domain of the present invention is capable of inhibiting or neutralizing any available tissue factor protein from inducing blood coagulation through the extrinsic coagulation pathway (see, Bach, R., (1988) CRC Crit. Rev. Biochem. 23:339–368). As will be appreciated by the skilled artisan the term "neutralize" is a relative term. Thus the term "neutralize" when used to describe the biological activity of the tissue factor domain of the present invention means a tissue factor protein variant that when added in a 10-fold molar excess to wild-type tissue factor in a standard chromogenic assay (see, Roy, S., (1991) J. Biol. Chem. 266:4665–4668, and O'Brien, D., et al., (1988) J. Clin. Invest. 82:206–212) produces at least a 50% inhibition of the conversion of Factor X to Factor Xa in the presence of Factor VII and other necessary reagents. Preferably the tissue factor domain will produce at least a 50% inhibition at a 5-fold molar excess and more preferably at least a 50% inhibition at a 2-fold molar excess. In a more preferred embodiment the tissue factor domain of the present invention will produce at least a 50% inhibition of the conversion of Factor X to Factor Xa when present in a 1:1 stoichiometric ratio with wild type tissue factor protein. According to the present invention, TF domains include but are not limited to full length, phosholipid associated tissue factor domains having both a transmembrane domain and a cytoplasmic domain as well as TF domains wherein all or a portion of the transmembrane and/or cytoplasmic domain of wild type tissue factor have been deleted. Accordingly, in determining the biological activity of a TF domain of the present invention in a chromogenic assay as described, the wild-type tissue factor corresponds in type to the particular TF domain being tested. Therefore a full length TF domain comprising all or a portion of the transmembrane domain of wild-type tissue factor and associated with a phospholipid is tested in a biological assay with wild type TF of the corresponding type comprising all or a portion of the transmembrane domain in a similar phospholipid environment. Likewise, a soluble TF domain wherein the transmembrane and cytoplasmic domain have been deleted is assayed with a wild-type TF domain wherein the transmembrane and cytoplasmic domain have been deleted.

It is a characteristic of the TF domain of the present invention that the protein bind FVII/FVIIa. Accordingly, the TF domain of the present invention shares those residues with wild type TF protein that are necessary for the binding of TF to FVII/FVIIa. By "bind to FVII/FVIIa" is meant that the TF domain of the present invention has the ability to bind to FVII/FVIIa to a degree that TF domain can compete for binding with wild type TF at physiological concentrations.

Preferred among the TF domains are those that have a KD for FVII/FVIIa of about between 10.0 picomolar (pM) and about 1 micromolar (μM) in a standard binding assay such as that described by Kelley et al., (1995) supra. More preferably the TF domain has a KD for FVII/FVIIa of about between 10 pM and 10 nanomolar (nM) and most preferably about between 10 pM and 1 nM.

The skilled artisan will recognize those residues in TF that contribute to the FVIIa binding (Kelley et al. (1995) supra; Gibbs et al., (1994) supra; Ruf et al., (1994) Biochemistry, 33, 1565–1572; Schullek et al., (1994) J. Biol. Chem. 269:19399–19403; Muller et al., (1994) 33:10864–10869). According to the present invention, the TF domain shares at least those residues with wild type TF which are required for FVIIa/FVII binding, as described. Preferably, the tissue factor domain will share at least about 80% sequence homology and more preferably between about 85%–95% sequence homology with wild-type tissue factor protein.

TF domains include but are not limited to full length, membrane bound or phosholipid associated tissue factor domains having both a transmembrane domain and a cytoplasmic domain. The TF domain also includes tissue factor domains wherein all or a portion of the transmembrane and/or cytoplasmic domain of wild type tissue factor have been deleted. Accordingly, the tissue factor domain of the molecule can be formulated as soluble protein having the carboxyl-terminal membrane anchor portion and cytoplasmic portion removed. Alternatively, a TF protein can be prepared as an integral membrane protein having a membrane anchor. The tissue factor domain having a complete membrane anchor domain is provided in association with phospholipid compositions such as liposome formulations.

Preferred among the TF domains of the present invention are those TF domains wherein all or a portion of the transmembrane and cytoplasmic domains of wild type tissue factor have been deleted. According to this aspect of the present invention, the TF domain comprises at least a portion of the N-terminal fibronectin type III domain of wild type tissue factor. Preferably, the TF domain comprises at least amino acids 1–102 of wild type tissue factor. More preferably the TF domain of the present invention comprises both fibronectin type III domains of wild type tissue factor. Preferably, according to this aspect of the present invention, at least amino acids 1–219 of wild type TF are present.

The TF domain of the present invention comprises a polypeptide which retains its ability to bind FVII/FVIIa and which is further capable of neutralizing the procoagulant activity of wild type tissue factor as described above. By way of illustration, substitution, insertion or deletions of particular amino acids along the length of wild type TF produce TF variants with reduced ability to act as a cofactor for FVIIa. The skilled artisan will recognize those residues of wild type TF which contribute to the procoagulant function of TF. For example, residues in the area of amino acids 157–168 contribute to the procoagulant function of TF-FVIIa (Kelley et al., (1995) supra; Ruf et al., (1992) supra) but are not important for FVII/FVIIa binding. According to the present invention any or all of these amino acids are selectively substituted or deleted to provide a TF domain that binds to FVII/FVIIa but is capable of neutralizing the procoagulant activity of wild type tissue factor.

In a preferred embodiment, any or all of residues Trp158, Lys159, Ser163, Gly164, Lys165, Lys166, and Tyr185 of wild type tissue factor are selectively substituted or deleted to provide a TF domain of the present invention. Preferred substitutions are described in U.S. Pat. No. 5,346,991 and include substitution with an amino acid other than one bearing a substantially positively charged side chain at physiological pH. Exemplary substitutions include any or all of Trp158Phe, Lys159Ala, Ser163Ala, Lys165Ala, Lys166Ala, and Tyr185Ala. In a most preferred aspect of the present invention, lysine residues 165 and 166 which are important to TF cofactor function but do not interfere with FVIIa complex formation (Roy et al., (1991) J. Biol. Chem. 266:22063; Ruf et al., (1992) J. Biol. Chem. 267:6375) are selectively substituted. Therefore, according to a preferred aspect of the present invention at least residues 165 and 166 of wild type tissue factor are selectively substituted to result in a molecule which retains its ability to bind FVII/FVIIa but has a reduced ability to act as a cofactor as described.

In a particular aspect, alanine substitution of these residues is preferred although any substitution which results in a decreased rate of FX activation catalyzed by the TF-FVIIa complex (Ruf et al., (1992) supra) is appropriate. Lysine residues 165 and 166 are located on the C-terminal fibronectin type III domain of TF on the opposite surface of the molecule from residues found to be important for FVIIa binding on the basis of mutagenesis results (Kelley et al., (1995) supra).

Preferred tissue factor domains of the present invention are those described in U.S. Pat. No. 5,346,991, entitled "Tissue Factor Mutants Useful for the Treatment of Myocardial Infarction and Coagulopathic Disorders" the disclosure of which is specifically incorporated herein by reference. This patent describes the generation of tissue factor variants that are capable of inhibiting the ability of endogenous tissue factor to induce coagulation. These variants have either or both of the positively charged amino acid residues 165 and 166 substituted with an α-amino acid other than one bearing a substantially positively charged side chain at physiological pH. The variants include human tissue factor molecules as described above having the cytoplasmic portion of wild type tissue factor, residues 244–263, removed, as well as the transmembrane region at residues 220–243. Any of the tissue factor variants may appropriately form the TF domain of the present invention. International Publication No. WO 94/28017 also describes TF variants that are able to bind FVII/FVIIa and have a reduced procoagulant cofactor activity. Most preferred among the molecules described therein are a tissue factor protein having an amino acid sequence homologous to a wild type tissue factor protein and wherein at least one amino acid associated with TF cofactor function is selectively substituted, deleted or replaced to result in a molecule which retains its ability to bind FVII/FVIIa but which has reduced ability to act as a cofactor as described above.

2. Active Site Domain

According to the present invention the "active site inhibitor domain" of the compositions may be selected from any one of several groups of Factor VIIa active site directed inhibitors. Such active site inhibitors are broadly categorized for the purpose of the present invention into i) active site inhibitors which reversibly bind the active site of FVIIa and are cleavable by Factor VIIa, ii) active site inhibitors which reversibly bind to the active site of Factor VIIa but cannot be cleaved, and iii) active site inhibitor molecules which irreversibly bind to the active site of Factor VIIa. For a review of inhibitors of serine proteinases see, *Proteinase Inhibitors* (Research Monographs in Cell and Tissue Physiology; v. 12) Elsevier Science Publishing Co., Inc., New York (1990).

According to the first group, active site inhibitor domains which reversibly bind to and are cleavable by the active site of Factor VIIa, the Kunitz and Kazal type serine protease inhibitors are preferred with the Kunitz type being most preferred. Reversible active site inhibitor domains bind to the active site of Factor VIIa through non-covalent interactions such as ionic bonds, hydrophobic interactions or hydrogen bonding. Kunitz domains are recognized by the skilled artisan to be slow tight binding reversible inhibitors of serine proteases.

Kunitz domain active site inhibitor domains of the present invention include any of the known mammalian Kunitz type domains and especially the Kunitz domain APPI (from human Alzheimer's disease amyloid β-protein precursor; Castro, M. et al. (1990) FEBS Lett. 267:207–212) residues 1–58; TFPI-KD1 (residues 22–79), TFPI-KD2 (residues 93–150), and TFPI-KD3 (residues 185–242) of human TFPI (tissue factor protein inhibitor or LACI, Broze Jr., G. J. et al., (1990) Biochemistry 29:7539–7546); ITI-KD1 and ITI-KD2, (residues 22–79 and 78–135) of human inter-α-trypsin inhibitor, respectively (Vetr, H. et al., (1989) FEBS Lett. 245:137–140); Collagen α 3 (VI) (residues 2899–2956) Collagen alpha 3 (VI) chain precursor (Chu, M. L. (1990) et al. EMBO J. 9:385–393); HKIB9 (7–60) Human Kunitz-type protease inhibitor, HKIB9 (Norris, K., in Genbank Database (Dec. 31, 1993, Release 39.0), submitted Jan. 19, 1994); BPTI (1–58), Aprotinin, bovine basic pancreatic trypsin inhibitor (Creighton T. E. and Charles, I. G., (1987) Cold Spring Harbor Symp. Quant. Biol. 52:511–519).

Preferred among the Kunitz-type serine proteases are those molecules which bind FVIIa active site with sufficient affinity to reversibly inhibit the molecule. By this is meant that the Kunitz-type domain is able to bind to and inhibit the catalytic activity of FVIIa as measured by routine assays such as those described (below). Such molecules have an apparent dissociation constant ($K_i^*$) with respect to TF-FVIIa of less than about 100 nM, more preferably the molecules have an apparent dissociation constant of less than about 10 nM. Most preferred among the Kunitz type domains are those that have a $K_i^*$ of less than about 5 nM for TF-Factor VIIa.

Apparent equilibrium dissociation constants ($K_i^*$) are determined using methods derived for tight-binding inhibitors (Bieth, J., (1974) Proteinase Inhibitors 463–469; Williams, J. W. and Morrison, J. F., (1979) Methods Enzymol 63:437–467), assuming enzyme and inhibitor form a reversible complex with a 1:1 stoichiometry as has been observed for the interaction of Kunitz-type domain with the FVIIa serine protease (Bode, W. and R. Huber, (1992) Eur. J. Biochem. 204:433–451; Laskowski, M., Jr. and I. Kato, (1980) Annu. Rev. Biochem. 49:593–626). The data are fit by nonlinear regression analysis to Equation 1:

$$V_i/V_o = 1 - \frac{[E_o] + [I_o] + K_i^* - \sqrt{([E_o] + [I_o] + K_i^*)^2 - (4 \cdot [E_o] \cdot [I_o])}}{2 \cdot [E_o]} \quad (1)$$

where $V_i/V_o$ is the fractional activity (steady-state inhibited rate divided by the uninhibited rate), $[E_o]$ is the total FVIIa concentration and $[I_o]$ is the total inhibitor concentration.

By way of example and not limitation, preferred Kunitz type domains have a 58 amino acid backbone structure, with amino acids 11–19 corresponding to primary binding loop which fits into the active site of the serine protease. Kunitz-type domains having a particular amino acid sequence within the primary binding loop demonstrate preferred inhibition as defined above. Exemplary Kunitz domains showing the preferred inhibition of factor VIIa as described above are Kunitz type domains with a Pro at position P5, a Gly at position P4, a Pro, Val, Leu, or Trp at position P3, a Cys at position P2, an Arg, Lys, or Met at position P1, an Ala at position P1', a Leu, Met or Ile at position P2', a Met, Ile, Leu or Tyr at position P3', and Leu, Lys or Arg at position P4'. Kunitz type domains also preferred according to the present invention also feature Phe, Val, Ile, Trp, or Tyr at position 34 (P19') a Cys at position 38 (P23') and a His, Tyr, or Gly at position 39 (P24').

Exemplary Kunitz type active site inhibitor domains are also described in International Publication No. WO 95/23860 and are represented by structural formula I:

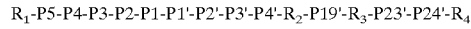

$R_1$-P5-P4-P3-P2-P1-P1'-P2'-P3'-P4'-$R_2$-P19'-$R_3$-P23'-P24'-$R_4$

According to this formula, when P5-P4', P19', P23', and P24'are selected as described above, $R_1$ is selected from APPI amino acids 1–10, VREVCSEQAE (SEQ ID NO: 1); TFPI-KD1 amino acids 22–31, MHSFCAFKAD (SEQ ID NO: 2); TFPI-KD2 amino acids 93–102, KPDFCFLEED (SEQ ID NO: 3); TFPI-KD3 amino acids 185–194, GPSWCLTPAD (SEQ ID NO: 4); ITI-KD1 amino acids 22–31, KEDSCQLGYS (SEQ ID NO: 5); ITI-KD2 amino acids 78–87, TVAACNLPIV (SEQ ID NO: 6); HKIB9 amino acids 1–10, LPNVCAFPME (SEQ ID NO: 7); and BPTI amino acids 1–10, RPDFCLEPPY (SEQ ID NO: 8).

$R_2$ is selected from APPI amino acids 20–33, RWYFDVTEGKCAPF (SEQ ID NO: 9); TFPI-KD1 amino acids 41–54, RFFFNIFTRQCEEF (SEQ ID NO: 10); TFPI-KD2 amino acids 112–125, RYFYNNQTKQCERF (SEQ ID NO: 11); TFPI-KD3 amino acids 204–217, RFYYNSVIGKCRPF (SEQ ID NO: 12); ITI-KD1 amino acids 41–54, RYFYNGTSMACETF (SEQ ID NO: 13); ITI-KD2 amino acids 97–110, LWAFDAVKGKCVLF (SEQ ID NO: 14); Collagen α 3(VI) amino acids 2918–2931, KWYYDPNTKSCARF (SEQ ID NO: 15); HK1B9 amino acids 20–33, RWFFNFETGECELF (SEQ ID NO: 16); and BPTI amino acids 20–33, RYFYNAKAGLCQTF (SEQ ID NO: 17).

$R_3$ is selected from the group YGG and YSG.

$R_4$ is selected from the group APPI amino acids 40–58 (Met52Ala), GNRNNFDTEEYCAAVCGSA (SEQ ID NO: 18); APPI amino acids 40–58, GNRNNFDTEEYCMAVCGSA (SEQ ID NO: 19); TFPI-KD1 amino acids 61–79, GNQNRFESLEECKKMCTRD (SEQ ID NO: 20); TFPI-KD2 amino acids 132–150, GNMNNFETLEECKNICEDG (SEQ ID NO: 21); TFPI-KD3 amino acids 224–242, GNENNFTSKQECLRACKKG (SEQ ID NO: 22); ITI-KD1 amino acids 61–79, GNGNNFVTEKECLQTCRTV (SEQ ID NO: 23); ITI-KD2 amino acids 117–135, GNGNKFYSEKECREYCGVP (SEQ ID NO: 24); Collagen α 3(VI) amino acids 2938–2956, GNENKFGSQKECEKVCAPV (SEQ ID NO: 25); HK1B9 amino acids 40–58, GNSNNFLRKEKCEKFCKFT (SEQ ID NO: 26); and BPTI amino acids 40–58, AKRNNFKSAEDCMRTCGGA (SEQ ID NO: 27);

In a preferred Kunitz type active site inhibitor domain $R_1$ has the sequence VREVCSEQAE (SEQ ID NO: 1) $R_2$ has the sequence RWYFDVTEGKCAPF (SEQ ID NO: 9) $R_3$ has the sequence YGG; and $R_4$ has the sequence:GNRNNFDTEEYCAAVCGSA (SEQ ID NO: 18) or GNRNNFDTEEYCMAVCGSA (SEQ ID NO: 19).

Therefore, preferred Kunitz type active site inhibitor domains include:

I-18 $R_1$PGVCRALILR$_2$FR$_3$CGR$_4$ (SEQ ID NO: 28)
I-49 $R_1$PGWCRALILR$_2$FR$_3$CGR$_4$ (SEQ ID NO: 29)
I-14 $R_1$PGFCRALILR$_2$FR$_3$CGR$_4$ (SEQ ID NO: 30)
I-16 $R_1$GGWCRALILR$_2$FR$_3$CGR$_4$ (SEQ ID NO: 31)
where $R_4$ is the sequence identified by SEQ ID NO: 19, and II-4 R$_1$PGPCRAMISR$_2$FR$_3$CYR$_4$ (SEQ ID NO: 32)
II-3 R$_1$PGWCRAMISR$_2$IR$_3$CGR$_4$ (SEQ ID NO: 33)
II-6 R$_1$PGPCKAMISR$_2$IR$_3$CWR$_4$ (SEQ ID NO: 34)
III-27 R$_1$TGPCRALISR$_2$WR$_3$CGR$_4$ (SEQ ID NO: 35)
III-30 R$_1$TGPCRALISR$_2$YR$_3$CGR$_4$ (SEQ ID NO: 36)
TF7I-VY R$_1$PGVCRALILR$_2$FR$_3$CYR$_4$ (SEQ ID NO: 37)
TF7I-LY R$_1$PGLCPALILR$_2$FR$_3$CYR$_4$ (SEQ ID NO: 38)
TF7I-WY R$_1$PGWCRALILR$_2$FR$_3$CYR$_4$ (SEQ ID NO: 39)
TF7I-PG R$_1$PGPCRALILR$_2$FR$_3$CGR$_4$ (SEQ ID NO: 40)
IV-47C R$_1$PGPCRAMMKR$_2$IR$_3$CHR$_4$ (SEQ ID NO: 41)
IV-54C R$_1$PGPCRALMKR$_2$VR$_3$CYR$_4$ (SEQ ID NO: 42)
IV-31B R$_1$PGPCRALMKR$_2$VR$_3$CFR$_4$ (SEQ ID NO: 43)
IV-49C R$_1$PGPCRAMMKR$_2$IR$_3$CYR$_4$ (SEQ ID NO: 44)
IV-50C R$_1$PGPCRAMYKR$_2$IR$_3$CYR$_4$ (SEQ ID NO: 45)
IV-57C R$_1$PGVCRAMMKR$_2$IR$_3$CGR$_4$ (SEQ ID NO: 46)
IV-51C R$_1$PGPCKALMRR$_2$YR$_3$CYR$_4$ (SEQ ID NO: 47)
IV-35B R$_1$PGPCKAIMKR$_2$IR$_3$CHR$_4$ (SEQ ID NO: 48)
IV-58C R$_1$PGPCKALMKR$_2$YR$_3$CHR$_4$ (SEQ ID NO: 49)
IV-48C R$_1$PGPCKALMKR$_2$WR$_3$CWR$_4$ (SEQ ID NO: 50)
IV-46C R$_1$PGPCKAMIKR$_2$LR$_3$CYR$_4$ (SEQ ID NO: 51)
IV-55C R$_1$PGPCKALMKR$_2$FR$_3$CYR$_4$ (SEQ ID NO: 52)
IV-32B R$_1$PGPCKALMKR$_2$YR$_3$CYR$_4$ (SEQ ID NO: 53)
IV-36B R$_1$PGPCKALMKR$_2$VR$_3$CYR$_4$ (SEQ ID NO: 54)
IV-40B R$_1$PGACKAMYKR$_2$IR$_3$CGR$_4$ (SEQ ID NO: 55)
53b R$_1$PGPGRALILR$_2$FR$_3$AYR$_4$ (SEQ ID NO: 56), and
TF7I-C R$_1$PGPCRALILR$_2$FR$_3$CYR$_4$ (SEQ ID NO: 57)
where R$_4$ has the sequence identified by SEQ ID NO: 18.

It will be appreciated by the skilled artisan that with a Kunitz type active site inhibitor domain all or a portion of the Kunitz type domain may be used as the active site inhibitor domain according to the present invention. Any portion of the Kunitz domain which binds with sufficient affinity to reversibly inhibit FVIIa will be sufficient as Factor VIIa active site domain. Such molecules generally comprise at least the P$_1$ and P$_1$' residues of the Kunitz domain and preferably the primary binding loop of the Kunitz domain P$_5$ through P$_4$'.

The active site inhibitor moiety of the present invention may also be an irreversible FVIIa serine protease inhibitor. Such irreversible active site inhibitor domains generally form covalent bonds with the Factor VIIa active site. Such irreversible inhibitors include general serine protease inhibitors such as peptide chloromethylketones (see, Williams et al., (1989) J. Biol. Chem. 264:7536–7540) or peptidyl chloromethanes; azapeptides; acylating agents such as various guanidinobenzoate derivatives and the 3-alkoxy-4-chloroisocoumarins; sulphonyl fluorides such as phenylmethylsulfonylflouride (PMSF), diisopropylflourophophate (DFP), tosylpropylchloromethyl ketone (TPCK) and tosyllysylchloromethylketone (TLCK); nitrophenylsulphonates and related compounds; heterocyclic protease inhibitors such as isocoumarins, and coumarins.

3. Linker

According to the present invention, the tissue factor domain is linked, preferably via its N-terminus to the FVII/FVIIa active site inhibitor domain of the hybrid molecule via a flexible linker domain. The linker component of the hybrid molecule of the invention does not necessarily participate in the binding of the molecule to FVII/FVIIa. Therefore, according to the present invention, the linker domain, is any group of molecules that provides a spatial bridge between the FVII/FVIIa active site inhibitor domain and the tissue factor domain of the molecule.

The linker domain can be of variable length and makeup, however, according to the present invention, it is the length of the linker domain and not its structure that is important. The linker domain preferably allows for the active site domain of the hybrid molecule to fit into the serine protease active-site groove of FVII/FVIIa while allowing the tissue factor domain of the molecule to bind to the TF binding site on the FVII/FVIIa molecule. Therefore, the length of the linker domain is dependent upon the character of the two "functional" domains of the hybrid molecule.

One skilled in the art will recognize that various combinations of atoms provide for variable length molecules based upon known distances between various bonds (Morrison, and Boyd, Organic Chemistry, 3rd Ed, Allyn and Bacon, Inc., Boston, Mass. (1977)). For example, the linker domain may be a polypeptide of variable length. The amino acid composition of the polypeptide determines the character and length of the linker. In a preferred embodiment, the linker molecule comprises a flexible, hydrophilic polypeptide chain. Exemplary, linker domains comprises one or more [(Gly)$_4$-Ser] units.

In a preferred aspect, the active site inhibitor domain is a Kunitz type serine protease inhibitor, the TF domain is hTFAA and the linker domain is a polypeptide comprising between 5 and about 35 amino acids and spanning a distance of greater than about 30 Å. More preferably, the linker comprises between about 20 and about 30 amino acids and spans a distance of greater than about 60 Å. Most preferably the linker comprises about a 22 to 27 amino acid polypeptide and is comprised of about 4 to 5 [(Gly)$_4$-Ser] units.

4. Synthesis

The hybrid molecules of the present invention may be synthesized by various techniques which are well known in the art. These include recombinant DNA techniques, solid phase synthesis, solution phase synthesis, organic chemical synthetic techniques or a combination of these techniques. The choice of synthesis will depend upon the particular molecule to be generated. For example, in one embodiment the hybrid molecule of the present invention is not entirely "protein" in nature and is synthesized by a combination of recombinant techniques and solution phase techniques.

For example, for the synthesis of hybrid molecules of the present invention which contain both amino acid or protein portions and non-protein portions the molecule is generally obtained by synthesizing the protein portion of the molecule by recombinant techniques as described below followed by coupling the non protein portion of the molecule to the protein portion via solid phase or solution phase methods.

For the coupling of protein and non protein portions of the molecule, chemical coupling is preferred. According to this procedure, traditional crosslinking agents are employed such as molecules having one or more reactive groups that can react with more than one sites on the protein and non-protein molecules. Biocompatable crosslinkers are preferred having the characteristics of being non-carcinogenic, nontoxic, and substantially nonimmunogenic in vivo. Typically the cross linker will covalently bond with an amino group or a sulfhydryl group on the protein portion of the molecule and a hydroxyl, amino, aldehyde or carboxylic acid group of the non-protein portion of the molecule. Methods of crosslinking molecules are reviewed by Means and Feaney (1990) Bioconjugate Chemistry, 1:2–12.

Various techniques are available which may be employed to produce DNA, which can encode proteins for the recombinant synthesis of hybrid proteins of the invention. For instance, it is possible to derive DNA based on naturally occurring DNA sequences that encode for changes in an amino acid sequence of the resultant protein. These mutant DNA can be linked together and used to obtain the hybrid molecules of the present invention. These techniques contemplate, in simplified form, obtaining a gene encoding a tissue factor domain and a gene encoding an active site inhibitor domain such as a Kunitz type domain of structural formula I; modifying the genes by recombinant techniques such as those discussed below; inserting the genes into an appropriate expression vector separated by a gene encoding a linker module of various lengths; inserting the vector into an appropriate host cell; culturing the host cell to cause expression of the hybrid molecule; and purifying the molecule produced thereby.

Somewhat more particularly, a DNA sequence encoding the bifunctional molecule of the present invention is obtained by synthetic construction of the DNA sequence (Sambrook, J. et al., Molecular Cloning (2nd ed.), Cold Spring Harbor Laboratory, New York, (1989).

By way of example, expression vectors encoding wild type tissue factor can be obtained and subject to site specific mutagenesis (Kunkel et al., (1991) Methods Enzymol. 204:125–139; Carter, P., et al., (1986) Nucl. Acids. Res. 13:4331; Zoller, M. J. et al., (1982) Nucl. Acids Res. 10:6487), cassette mutagenesis (Wells, J. A., et al., (1985) Gene 34:315), or restriction selection mutagenesis (Wells, J. A., et al., (1986) Philos. Trans, R. Soc. London Ser A 317, 415) to obtain the tissue factor domain of the molecule. The mutant DNA can then be used by insertion into expression vectors containing DNA encoding an active site inhibitor domain. A DNA sequence encoding a linker domain of varying length such as one or more [(Gly)$_4$-Ser] units can then be inserted into the same expression vector.

Oligonucleotide-mediated mutagenesis is a preferred method for preparing the DNA encoding the tissue factor variants and the Kunitz type active site inhibitor domains of the present invention. This technique is well known in the art as described by Adelman et al., (1983) DNA, 2:183. Briefly, the native or unaltered DNA of a wild type tissue factor or Kunitz type domain, for instance APPI, is altered by hybridizing an oligonucleotide encoding the desired mutation to a DNA template, where the template is the single-stranded form of a plasmid or bacteriophage containing the unaltered or native DNA sequence.

The DNA encoding variants are then inserted into an appropriate plasmid or vector separated by DNA sequence encoding a linker domain. The vector is used to transform a host cell. In general, plasmid vectors containing replication and control sequences which are derived from species compatible with the host cell are used in connection with those hosts. The vector ordinarily carries a replication site, as well as sequences which encode proteins that are capable of providing phenotypic selection in transformed cells.

For example, E. coli may be transformed using pBR322, a plasmid derived from an E. coli species (Mandel, M. et al., (1970) J. Mol. Biol. 53:154). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-lambda represent expression vectors with the tac, trp, or P$_L$ promoters that are currently available (Pharmacia Biotechnology).

Other preferred vectors can be constructed using standard techniques by combining the relevant traits of the vectors described herein. Relevant traits of the vector include the promoter, the ribosome binding site, the variant gene or gene fusion, the signal sequence, the antibiotic resistance markers, the copy number, and the appropriate origins of replication.

In E. coli, Kunitz domains have been expressed as intact secreted proteins (Castro, M. et al., (1990) FEBS Lett. 267:207–212), intracellularly expressed proteins (Altman, J. D. et al., (1991) Protein Eng. 4:593–600), or as fusion proteins (Sinha, S. et al., (1991) J. Biol. Chem. 266:21011–21013; Lauritzen, C. et al., (1991) Prot. Express. Purif. 2:372–378; Auerswald, E. A. et al., (1988) Biol. Chem. Hoppe-Seyler 369:27–35).

The host cell may be prokaryotic or eukaryotic. Prokaryotes are preferred for cloning and expressing DNA sequences to produce parent polypeptides, segment substituted polypeptides, residue-substituted polypeptides and polypeptide variants. For example, E. coli K12 strain 294 (ATCC No. 31446) may be used as E. coli B, E. coli X1776 (ATCC No. 31537), and E. coli c600 and c600hfl, E. coli W3110 (F-, gamma-, prototrophic/ATCC No. 27325), bacilli such as Bacillus subtilis, and other enterobacteriaceae such as Salmonella-typhimurium or Serratia marcesans, and various pseudomonas species. The preferred prokaryote is E. coli W3110 (ATCC 27325). When expressed by prokaryotes the polypeptides typically contain an N-terminal methionine or a formyl methionine and are not glycosylated. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure (Tissue Culture, Academic Press, Kruse and Patterson, eds. [1973]). Examples of such useful host cell lines are VERO and HeLa cells, Chinese Hamster Ovary (CHO) cell lines, W138, 293, BHK, COS-7 and MDCK cell lines. Yeast expression systems have been used to make Kunitz domains (Wagner, S. L. et al., (1992) Biochem. Biophys. Res. Commun. 186:1138–1145; Vedvick, T. et al., (1991) J. Indust. Microbiol. 7:197–202). In particular the yeast Pichia pastoris has been used successfully using the Saccharomyces cerevisiae α mating factor prepro signal sequence and the P. pastoris alcohol oxidase AOX1 promoter and terminator sequences. Other yeast expression vectors and hosts commonly used to express heterologous proteins are also contemplated.

5. Compositions

The hybrid molecule of the present invention comprising a TF domain and a FVIIa active site domain is typically provided in a compositional form that is suitable for its intended use. The hybrid molecule of the present invention comprising a TF domain can be prepared in the soluble form such as the hTFAA form described herein. According to this aspect of the invention the tissue factor domain of the molecule is prepared without a membrane anchor. Alternatively, the tissue factor domain can be prepared as a full-length membrane-associated form, with the membrane anchor present.

The hybrid molecule of the present invention may also comprise a TF domain comprising all or a portion of the transmembrane domain of wild type tissue factor. It is preferred, according to the present invention, that bifunctional molecules comprising a TF domain containing a membrane anchor domain be formulated in a composition comprising a mild detergent or phospholipid (PL). Although the composition of the present invention comprising a full-length TF domain including a membrane anchor or transmembrane domain retain their biological activity they are preferably formulated in a phospholipid composition. International Publication No. WO 94/28017 describes the preparation of phospholipid compositions comprising a TF domain that are appropriate for the compositions of the present invention.

Preferred compositions described in WO 94/28017 and suitable for the pharmaceutical compositions of the present invention are phospholipid compositions which afford maximum stability and biological activity for the composition. Such phospholipid compositions are preferably formulated to form liposome compositions, as are generally well known in the art. As described, suitable phospholipids for use in the liposome compositions of the present invention include those which contain fatty acids having twelve to twenty carbon atoms; said fatty acids may be either saturated or unsaturated. Preferred phospholipids for use according to the present invention include phosphatidylcholine (PC), phosphatidylethanolamine (PE), phosphatidylglycerol (PG) and phosphatidylserine (PS). These phopholipids may come from any natural source and the phospholipids, as such, may be comprised of molecules with differing fatty acids. Phospholipid mixtures comprising phospholipids from different sources may be used. For example, PC, PG and PE may be obtained from egg yolk; PS may be obtained from animal brain and spinal chord. These phospholipids may come from synthetic sources as well. The phospholipids are conveniently combined in the appropriate ratios to provide the phospholipid mixture for use in preparing the composition of the present invention. The preparation of liposomes is generally well known and has been previously described. Exemplary methods for preparation of liposomes includes reverse loading of liposomes (see U.S. Pat. No. 5,104,661), or in the manner described for the incorporation of amphotericin B into lipid vesicles. (See, e.g., Lopez-Berenstein et al., (1985) J. Infect. Dis., 151:704–710; Lopez-Berenstein, (1987) Antimicrob. Agents Chemother., 31:675–678; Lopez-Berenstein et al., (1984) J. Infect. Dis., 150:278–283; and Mehta et al., (1984) Biochem. Biophys. Acta, 770:230–234). Liposomes with enhanced circulation time may also be prepared as described in U.S. Pat. No. 5,013,556.

Thus, in one embodiment, the present invention contemplates the preparation of the hybrid molecules in the form of liposomes having TF domain portion of the molecule associated with the lipid bilayer of the liposomes, such that the TF membrane anchor domain is inserted through the lipid bilayer.

Other suitable compositions of the present invention comprise any of the above noted compositions with a pharmaceutically acceptable carrier, the nature of the carrier differing with the mode of administration, for example, in oral administration, usually using a solid carrier and in I.V. administration, a liquid salt solution carrier.

The compositions of the present invention include pharmaceutically acceptable components that are compatible with the subject and the protein of the invention. These generally include suspensions, solutions and elixirs, and most especially biological buffers, such as phosphate buffered saline, saline, Dulbecco's Media, and the like. Aerosols may also be used, or carriers such as starches, sugars, microcrystalline cellulose, diluents, granulating agents, lubricants, binders, disintegrating agents, and the like (in the case of oral solid preparations, such as powders, capsules, and tablets).

As used herein, the term "pharmaceutically acceptable" generally means approved by a regulatory agency of the Federal or a state government or listed in the U.S. Pharmacopeia or other generally recognized pharmacopeia for use in animals, and more particularly in humans.

The formulation of choice can be accomplished using a variety of the aforementioned buffers, or even excipients including, for example, pharmaceutical grades of mannitol, lactose, starch, magnesium stearate, sodium saccharin cellulose, magnesium carbonate, and the like. "PEGylation" of the compositions may be achieved using techniques known to the art (see for example International Patent Publication No. W092/16555, U.S. Pat. No. 5,122,614 to Enzon, and International Patent Publication No. WO 92/00748). Oral compositions may be taken in the form of solutions, suspensions, tablets, pills, capsules, sustained release formulations, or powders.

6. Therapeutic methods

The bifunctional molecules of the present invention can be used therapeutically to prevent the biological activity of the TF-FVIIa complex. The inhibition of TF-FVIIa is desirable in indications where the reduction of TF-FVIIa dependent coagulation is implicated. These situations include but are not limited to the prevention of arterial rethrombosis in combination with thrombolytic therapy. It has been suggested that the TF-FVIIa plays a significant role in a variety of clinical states including deep venous thrombosis, arterial thrombosis, stroke, DIC, septic shock, cardiopulmonary bypass surgery, adult respiratory distress syndrome, hereditary angioedema. Inhibitors of TF-FVIIa may therefore play important roles in the regulation of inflammatory and/or thrombotic disorders.

Thus the present invention encompass a method for preventing TF-FVIIa mediated event in a human comprising administering to a patient in need thereof a therapeutically effective amount of the hybrid molecule of the present invention. A therapeutically effective amount of the hybrid molecule of the present invention is predetermined to achieve the desired effect. The amount to be employed therapeutically will vary depending upon therapeutic objectives, the routes of administration and the condition being treated. Accordingly, the dosages to be administered are sufficient to bind to available FVII/FVIIa and form an inactive complex leading to decreased coagulation in the subject being treated.

The therapeutic effectiveness is measured by an improvement in one or more symptoms associated with the TF-FVIIa dependant coagulation. Such therapeutically effective dosages can be determined by the skilled artisan and will vary depending upon the age condition, sex and condition of the subject being treated. Suitable dosage ranges for systemic administration are typically between about 1 $\mu$g/kg to up to 100 mg/kg or more and depend upon the route of administration. According to the present invention a preferred therapeutic dosage is between about 1 $\mu$g/kg body weight and about 5 mg/kg body weight. For example, suitable regimens include intravenous injection or infusion sufficient to maintain concentration in the blood in the ranges specified for the therapy contemplated.

Pharmaceutical compositions which comprise the polypeptides of the invention may be administered in any suitable manner, including parental, topical, oral or local (such as aerosol or transdermal) or any combination thereof. Suitable regimens also include an initial administration by intravenous bolus injection followed by repeated doses at one or more intervals.

Where the composition of the invention is being administered in combination with a thrombolytic agent, for example, for the prevention of reformation of an accluding thrombus in the course of thrombolytic therapy, a therapeutically effective dosage of the thrombolytic is between about 80 and 100% of the conventional dosage range. The conventional dosage range of a thrombolytic agent is the daily dosage used in therapy and is readily available to the treating physician. (Physicians Desk Reference 1994, 50th Edition, Edward R. Barnhart, publisher). The typical dosage range will depend upon the thrombolytic being employed and include for tissue plasminogen activator (t-PA), 0.5 to about 5 mg/kg body weight; streptokinase, 140,000 to 2,500,0000 units per patient; urokinase, 500,000 to 6,250,000 units per patient; and anisolated streptokinase plasminogen activator complex (ASPAC), 0.1 to about 10 units/ kg body weight.

The term combination as used herein includes a single dosage form containing at least the molecule of the present invention and at least one thrombolytic agent. The term is also meant to include multiple dosage forms wherein the molecule of the present invention is administered separately but concurrently by two separate administration, such as in sequential administration. These combinations and compositions work to dissolve or prevent the formation of an occluding thrombus resulting in dissolution of the occluding thrombus.

According to a further aspect of the invention the hybrid molecule may be employed in preventing ex vivo coagulation such as that encountered in the extracorporeal perfusion of blood through for example artificial valves, prothesis, stents or catheters. According to this aspect of the invention the extracorporeal devise may be coated with the compositions of the invention resulting a lower risk of clot formation due to extrinsic pathway activation.

The following examples are offered by way of illustration and not by way of limitation. The disclosures of all citations in the specification are expressly incorporated herein by reference.

EXAMPLES

Materials

Human Factor VIIa, Factor X, Factor Xa, were purchased from Haematologic Technologies Inc. (Essex Jct., Vt.). Membrane tissue factor (mTF) was prepared by sonication of a human embryonic kidney cell line (293) expressing recombinant, full length (residues 1–263) human TF (Paborsky, L. R. et al., (1990) Protein Engineering 3:547–553). Bovine trypsin, 4-methylumbelliferyl p-guanidinobenzoate and CHAPS were purchased from Sigma Chemicals, Inc. Bovine serum albumin (BSA), Fraction V was obtained from Calbiochem (La Jolla, Calif.). $N^\alpha$-Benzoyl-L-arginine-p-nitroanilide was purchased from Bachem California (Torrance, Calif.). Human plasmin, S-2302, S-2251 and S-2366 were purchased from Kabi Vitrum (Sweden) and SPECTROZYME™ FXa was purchased from American Diagnostica (Greenwich, Conn.) and CHROMOZYM™ t-PA was from Boehringer Mannheim. All other reagents were of the highest grade commercially available.

Example 1
Construction and Expression of Fusion Proteins

Figure 3:
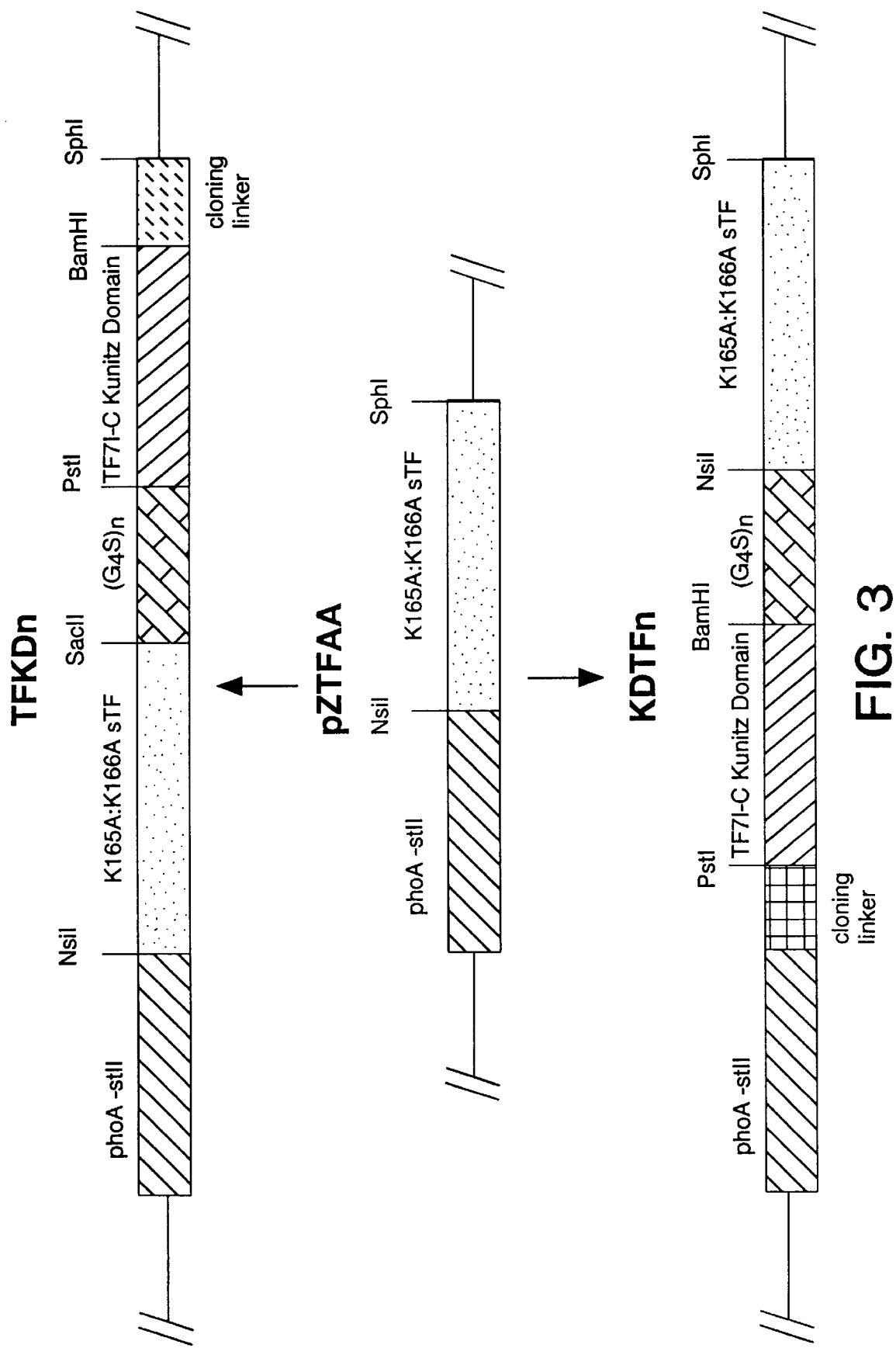
FIG. 3 depicts a schematic diagram of the construction of the fusion gene for the bacterial expression of a representative hybrid protein composition. Only the fusion gene and promotor regions of the plasmid are shown. The fusion genes were constructed by ligating the Pst/BamH1 fragment encoding the TF7I-C Kunitz-type domain with pZTFAA and oligonucleotides prepared by chemical synthesis.

Plasmids encoding tissue factor-Kunitz domain fusion proteins were constructed from the plasmid pZTFAA (Kelley, R. F. et al., (1995) Biochemistry 34:10383–10392) designed for expression of hTFAA by secretion from E. coli. As shown in FIG. 3, the expression unit of pZTFAA has the stII signal sequence joined to the N-terminus of hTFAA and transcription is driven by the alkaline phosphatase promoter (phoA). pZTFAA also has elements necessary for replication of the plasmid in single or double stranded form. The coding sequence for the TF7I-C Kunitz domain was excised from the plasmid pA4G32-TF7I-C (Dennis, M. S. & Lazarus, R. A. J. Biol. Chem. (1994) 269:22129–22136) by restriction enzyme digest with PstI and BamHI. For construction of genes encoding fusion proteins with the Kunitz domain joined to the C-terminus of hTFAA, a SacII restriction enzyme site was introduced into pZTFAA by oligonucleotide-directed mutagenesis (Kunkel, T. A. et al., Methods in Enzymology, (1987) 154:367–382). The resulting plasmid was digested with SacII and SphI, and then ligated with the PstI/BamHI fragment of the Kunitz domain and two oligonucleotide linkers prepared by chemical synthesis. One linker has SacII/PstI cohesive ends and encodes a single copy of the $G_4S$ module and was designed to fuse hTFAA in the correct reading frame with the N-terminus of the Kunitz domain. The second linker has BamHI/SphI cohesive ends and supplies the stop codon of the construct. For construction of fusion protein genes having a Kunitz domain attached to the N-terminus of hTFAA, pZTFAA was cleaved with NsiI which cuts the DNA at the junction between the stII and hTFAA segments. The NsiI cut plasmid was ligated with the PstI/BamHI Kunitz domain fragment and two oligonucleotide linkers prepared by chemical synthesis. One linker had Nsi/PstI cohesive ends thus joining the Kunitz domain in frame with the stII signal sequence. The second linker has BamHI/NsiI cohesive ends, encodes a single $G_4S$ module, and joins the Kunitz domain in frame with the N-terminus of hTFAA. The stop codon is derived from pZTFAA. Fusion genes having multiple copies of the $G_4S$ module were constructed by inserting chemically synthesized oligonucleotides encoding the $(G_4S)_n$ unit between the appropriate restriction enzyme sites in TFKD1 or KDTF1. For TFKD1, the SacII/PstI sites were used, and for KDTF1, the BamHI/NsiI sites were used. All fusion genes were confirmed by dideoxynucleotide sequencing (Sanger, F. et al., PNAS (USA) (1977)74:5463–5467).

Phagemids encoding the fusion proteins were transformed into E. coli strain 33B6, a derivative of E. coli W3110, for expression. Overnight saturated cultures were used to inoculate (1%) 10 L of media in a fermentation tank. Fermentation was performed as described previously (Carter, P. et al., Bio/Technology, (1992)10:163–167) except that the temperature was 30° C. rather than 37° C. Fusion proteins were secreted into the periplasm by virtue of the stII signal sequence. Cells were harvested by centrifugation 32 hours after inoculation and stored frozen at −20° C.

Example 2
Purification of Fusion Proteins

Figure 4:
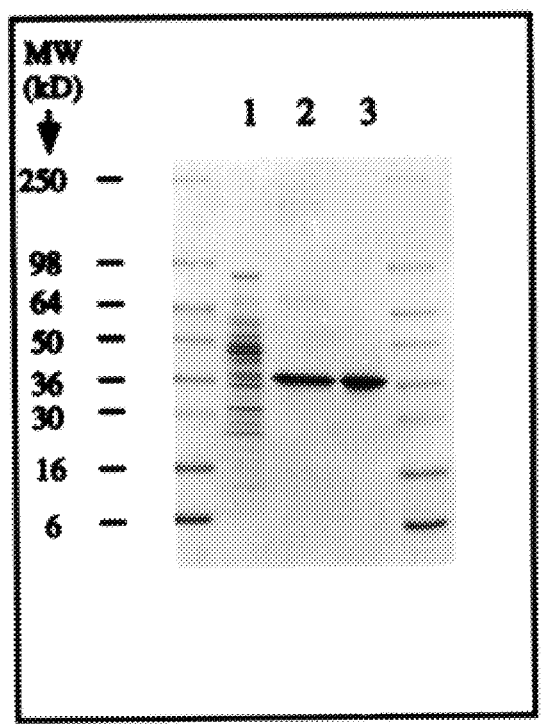
FIG. 4 depicts a rendering of a representative polyacrylamide gel showing samples obtained from the various purification steps for a representative hybrid molecule including freeze-thawing, then osmotically shocking, cells to obtain a periplasmic shockate (lane 1), immunoaffinity chromatography using D3 monoclonal anti-tissue factor antibody to isolate TF-containing proteins (lane 2), followed by size exclusion chromatography to remove high molecular weight species (lane 3).

Fusion proteins were extracted from E. coli cell paste and purified by immunoaffinity chromatography on an anti-TF monoclonal antibody (D3) column (Paborsky, L. R. et al., Biochemistry (1989) 28:8072–8077) as described for mutants of soluble tissue factor (Kelley, R. F. et al., (1995) Biochemistry 34:10383–10392). In some cases, a final size exclusion chromatography step, using a Superdex 75 (Pharmacia) column equilibrated with phosphate-buffered saline, was incorporated to purify fusion protein monomers from higher mass oligomers. The course of the fusion protein purification was followed by SDS-PAGE as shown in FIG. 4. This procedure yielded highly purified fusion protein. Each purified sample was submitted for analysis on a Sciex API 3 mass spectrometer equipped with an articulated electrospray source to verify that protein mass was consistent with the desired molecular composition. Multiply charged ions of horse myoglobin (MW=16,951 Da) were used for instrument calibration. Results of the analysis by mass spectrometry are shown in Table I and indicate that the fusion proteins have the expected molecular composition. Concentrations of the purified fusion proteins were determined by three methods (Table I): 1) Detection of hTFAA with the D3 antibody, 2) determination of Kunitz domain by titration of trypsin, and 3) absorbance measurements to determine total protein concentration. All three methods gave similar concentrations. Taken together with the mass spectrometry data these results show that the fusion proteins are intact and that both the Kunitz domain and TF domains are functional when present in the fusion protein.

The fusion proteins tested are listed below in Table I using shorthand notation KDTFn or TFKDn, wherein n is an integer referring to the number of $G_4S$ linker units. According to that notation TF refers to hTFAA. KD refers to the TF7I-c Kunitz domain. KD following TF (TFKD1) refers to a fusion protein wherein the KD domain is linked at its N-terminus via the peptide linker to the C-terminus of hTFAA. TF following KD (KDTF) refers to a fusion protein wherein the KD C-terminus is linked via the peptide linker to the N-terminus of the hTFAA.

TABLE I

| Fusion Protein Species | Mass Predicted | Mass Observed | D3 binding-based TF conc. | Trypsin inhibition-based KD conc. | Total protein conc. ($A_{280}$) |
|---|---|---|---|---|---|
| TFKD1 | 31440 | 31446 ± 5 | 28 µM | 29 µM | 28 µM |
| KDTF1 | 31511 | 31515 ± 5 | 74 µM | 77 µM | 76 µM |
| KDTF2 | 31826 | 31829 ± 2 | 66 µM | 64 µM | 66 µM |
| KDTF3 | 32142 | 32146 ± 4 | 36 µM | 38 µM | 36 µM |
| KDTF4 | 32457 | 32456 ± 3 | 37 µM | 35 µM | 31 µM |
| KDTF5 | 32772 | 32774 ± 5 | 20 µM | 17 µM | 16 µM |
| KDTF6 | 33087 | 33088 ± 4 | 28 µM | 22 µM | 39 µM |
| KDTF7 | 33403 | ND | 33 µM | 28 µM | 47 µM |

TABLE 1. Characterizations of purified fusion proteins. Predicted masses for fusion proteins in their native disulfide-bonded conformations are shown in Column 2. Results of mass spectral analyses are shown in Column 3. Columns 4–6 are concentration determinations based on binding to D3 monoclonal antibody immobilized in a BIAcore™ flow cell (an assay for TF domain structural/functional integrity), trypsin inhibition (an assay for Kunitz domain structural/functional integrity), and absorbance at 280 nm (total protein), respectively, for representative preparations of each fusion protein. ND=not determined.

Example 3
Fusion proteins inhibit TF-FVIIa-dependent factor X activation

The relative potency of the fusion proteins for inhibiting the catalytic function of the membrane tissue factor (mTF)-Factor VIIa (mTF-FVIIa) complex was evaluated by using an assay of FX activation. In this assay, FX is added to a solution of mTF-FVIIa and the rate of FXa formation is determined by removing aliqouts at various times, quenching the reaction by addition of EDTA to chelate calcium, and then measuring the amount of FXa formed by using the FXa specific substrate SPECTROZYME™ FXa. FXa cleavage of SPECTROZYME™ FXa does not require calcium. Hydrolysis of SPECTROZYME™ FXa is monitored by absorbance measurements at 405 nM. The rate may be used to calculate the FXa concentration by reference to a standard curve constructed with purified FXa. FX activation assays were conducted in a microtiter format and absorbance changes were monitored on an SLT EAR340AT plate reader controlled by a Macintosh IIci computer equipped with DeltaSoftII software (Biometallics). Nonlinear regression analysis was carried out using KaleidaGraph v3.01 (Synergy Software).

Activation assays used mTF, FVIIa and FX at final concentrations of 500 pM, 100 pM and 190 nM, respectively, in a volume of 200 µL. Inhibitor, if added, was present at a final concentration of 1 nM. This solution also contained 50 mM Tris-HCl pH 8, 150 mM NaCl, and 5 mM $CaCl_2$. The concentration of a stock solution of FVIIa was determined by active site titration with a quantitated sample of TF7I-C and by using CHROMOZYM™ t-PA as the substrate for FVIIa. The concentration of TF7I-C had been accurately determined by titration with trypsin that had been active site-titrated using 4-methylumbelliferyl p-guanidinobenzoate (Jameson, G. W. et al., (1973) Biochem. J. 131:107–117). After a 1 h incubation of 80 nM trypsin plus an aliquot of diluted inhibitor in 50 mM Tris, pH 8.0, 100 mM NaCl, 10 mM $CaCl_2$, and 0.05% TRITON™ X-100 at room temperature, 20 µl of 5 mM N-benzoyl-L-arginine-p-nitroanilide was added to a total volume of 150 µl. The change in absorbance at 405 nm was then monitored. The concentrations determined assumed a 1:1 stoichiometry of inhibitor with trypsin or FVIIa. The concentration of mTF was then determined from the increase in the rate of CHROMOZYM™ t-PA hydrolysis upon addition to a solution of the active site quantitated FVIIa. The concentration of FX and FXa was that supplied by the manufacturer.

In tests of the inhibitory properties of the fusion proteins, FVIIa was incubated with the fusion protein for 1 hour at 37° C. prior to addition of mTF. After adding mTF, incubation at 37° C. was continued for another hour before adding the substrate FX. Timing of the reaction began with substrate addition and 25 µL aliqouts were removed at various times and mixed with an equal volume of 50 mM EDTA. The amount of FXa formed was measured by adding Factor Xa buffer (10X=0.2 M HEPES pH 7.4, 1.5M NaCl, 0.25M EDTA, 1% PEG-8000) to a final concentration of 1× followed by 0.5 mM SPECTROZYME™ FXa. The final volume for each time point was 200 µL and the rates of SPECTROZYME™ FXa hydrolysis were monitored by changes in the absorbance at 405 nm and are reported in mOD/min.

Figure 5:
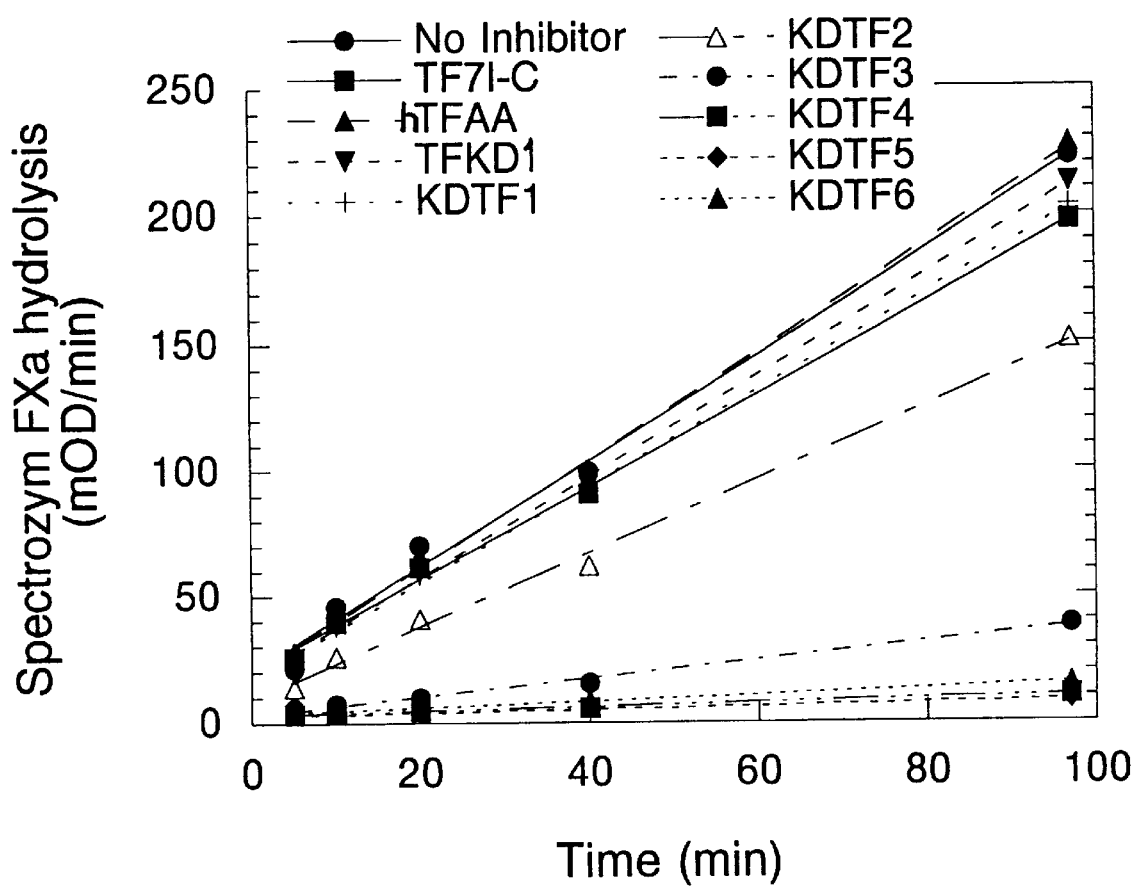
FIG. 5 depicts the effect of fusion proteins with 1 to 6 linker modules (KDTF1–-KDTF6) on TF-FVIIa-dependant FX activation. Fusion protein inhibition of TF-FVIIa interactions was quantified in a FX activation assay. The assay was performed by incubating 100 pM FVIIa with 1 nM inhibitor in TBS, pH 7.5, containing 5 mM CaCl$_2$ for 1 hr, then adding ½oth volume of a solution containing 10 nM membrane-bound TF. After further incubation for 1 hr, FX was added to 190 nM. At appropriate times, aliquots were removed and the reaction quenched with an equal volume of 50 mM EDTA. Activated FXa in quenched samples was then quantified using SPECTROZYME™-FXa as chromogenic substrate.

The effect of 1 nM inhibitors on FX activation catalyzed by mTF-FVIIa is shown in FIG. 5. At a 1 nM concentration of either TF7I-C or hTFAA alone, the rate of FXa generation is equivalent to that observed in the uninhibited control. Fusion proteins KDTF1 and TFKD1 also had little effect on the rate of FX activation. In contrast, KDTF2 gave a slight inhibition of FX activation. The extent of inhibition increased for fusion proteins with a longer linker and complete inhibition was observed with the KDTF5 fusion protein. KDTF4 appeared to be equipotent with KDTF5 whereas KDTF6 and KDTF7 were slightly weaker inhibitors. These data show that a potent inhibitor can be obtained by joining the Kunitz domain and hTFAA domains with a linker of appropriate length. The best linker in this series has 4 or 5 $G_4S$ modules corresponding to a polypeptide chain length, in extended conformation, of 45–60 Å.

Example 4
Determination of Equilibrium Dissociation Constants

Figure 6:
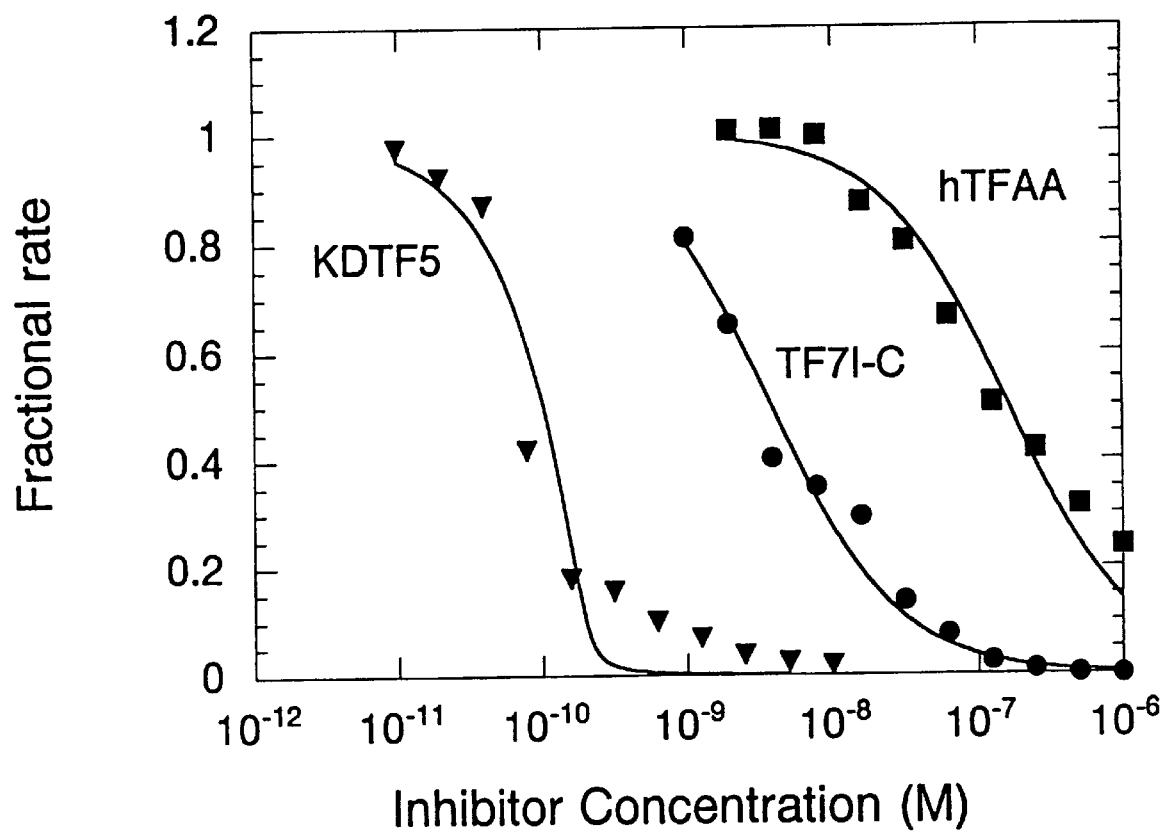
FIG. 6 depicts the inhibition of TF-FVIIa by a representative hybrid molecule KDTF5 (▼), a soluble K165A, K166A TF mutant (hTFAA) (■), and TF7I-C, a Kunitz-type serine protease inhibitor (●) for TF-FVIIa. Values were determined in a modified FX activation assay, performed with 2-fold more concentrated FVIIa and membrane-TF, and with varying inhibitor concentrations. $K_i^*$ determinations were made by fitting the fractional rate vs. inhibitor concentration data to equation 1 (infra).

The apparent equilibrium dissociation constant ($K_i^*$) for inhibition of FX activation was determined for hTFAA, TF7I-C and KDTF5. These experiments were conducted as described for Example 3 except that the FVIIa and mTF concentrations were 200 pM and 1 nM, respectively, and the inhibitor concentration was varied. A standard curve was constructed for SPECTROZYME™ FXa hydrolysis by purified FXa (Hematech) such that the observed rate of hydrolysis for each time point could be converted into a concentration of FXa generated. These data were then analyzed by least squares linear regression to calculate the initial velocity of FXa generation for each concentration of inhibitor. Initial velocities were compared to the uninhibited rate to yield a fractional rate of FX activation for each inhibitor concentration. These values are plotted in FIG. 6. Nonlinear regression analysis by using equation 1 provided the $K_{i1}*$ values of 160±19 nM, 3.8±0.5 nM, and 2±6 pM for hTFAA, TF7I-C, and KDTF5, respectively. It is clear that fusion of hTFAA and TF7I-C with a linker having an estimated length of 60 Å increases the inhibitor potency by at least 100-fold.

Equation 1:

$$V_i/V_o = 1 - \frac{[E_o] + [I_o] + K_i^* - \sqrt{([E_o] + [I_o] + K_i^*)^2 - (4 \cdot [E_o] \cdot [I_o])}}{2 \cdot [E_o]} \quad (1)$$

In this equation $[E_0]$ is the enzyme concentration, $[I_0]$ is the inhibitor concentration, $V_i$ is the initial velocity of FXa generation in the presence of $[I_0]$ and $V_0$ is the initial velocity in the absence of inhibitor.

Example 5

Coagulation Assays

Clotting times were measured using the ACL 300 Research Coagulation Analyzer. For the prothrombin time (PT) assays, the incubation time was set at 120 sec and acquisition time at 600 sec. Membranes from 293 cells expressing full length TF (Paborsky, L. R. et al., (1989) Biochemistry 28:8072–8077) were premixed with 25 mM $CaCl_2$. Citrated normal human plasma and inhibitor were incubated together for at least 5 minutes prior to assay. The sample (plasma and inhibitor) and reagent ($CaCl_2$/TF) were automatically mixed together after a 2 min incubation at 37° C. The clotting time was determined by optical assessment. Final concentrations were 0.028 to 5.6 $\mu$M inhibitor, 0.5 nM mTF, 12.5 mM $CaCl_2$, and 50% plasma in a total volume of 160 $\mu$L.

For the activated partial thromboplastin time (APTT) assays, the activation time was set at 70 sec and acquisition time at 360 sec. Citrated normal human plasma and inhibitor were incubated together for at least 5 minutes prior to assay. The sample (plasma and inhibitor) and activator (Instrumentation Laboratories Cephalin+Activator APTT Reagent) were automatically pipetted and incubated together for 70 sec at 37° C., then $CaCl_2$ was added and clotting time determined by means of optical assessment. Final concentrations were 0.028 to 5.6 $\mu$M inhibitor, 10% activator, 10.0 mM $CaCl_2$, and 50.0% plasma in a total volume of 200 $\mu$L.

Results

Figure 7:
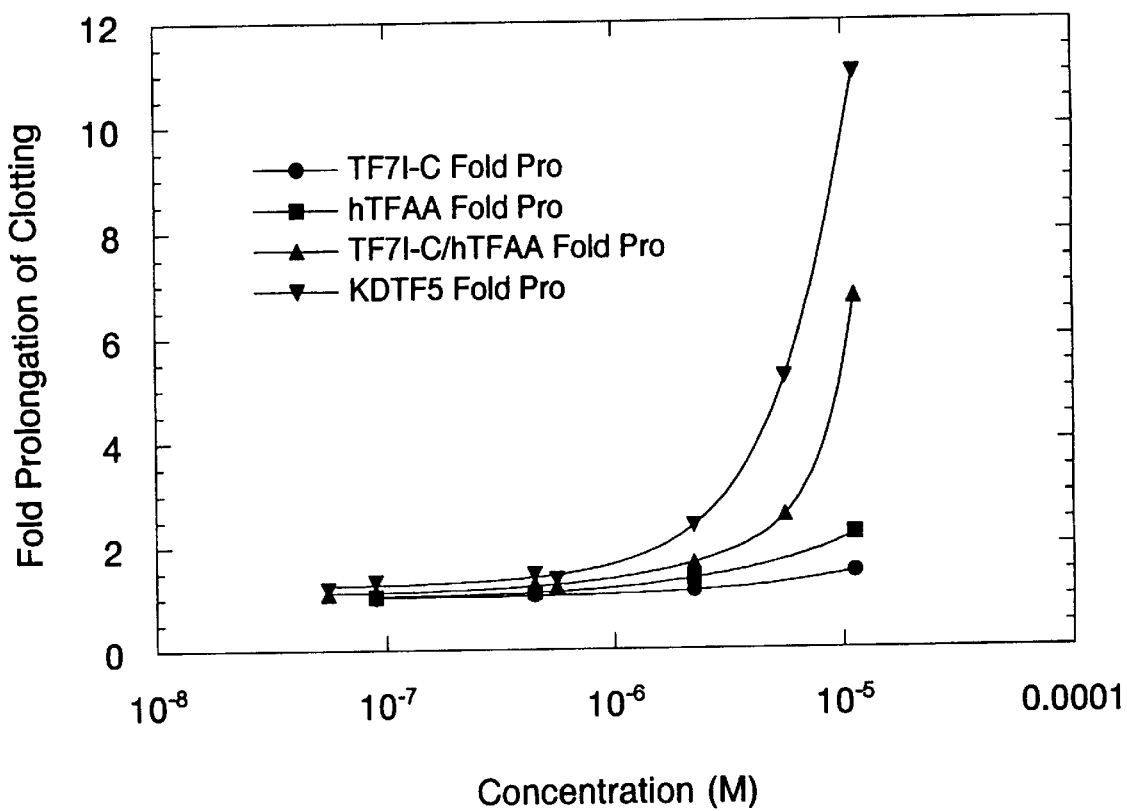
FIG. 7 depicts the effects of TF-FVIIa inhibitors on the clotting time determined in a prothrombin (PT) time assay. Coagulation was initiated by mixing citrated human plasma containing inhibitor with an equal volume of a solution containing membrane-bound TF (mTF) and $CaCl_2$. Fold-prolongation of clotting time was defined as the clotting time in the presence of inhibitor divided by the clotting time in its absence (PBS control). This latter time was 53.2±2.7 seconds. Data are shown for KDTF5 (▼), TF7I-C (●), hTFAA (■), and an equimolar mixture of TF7I-C and hTFAA (▼).
Figure 8:
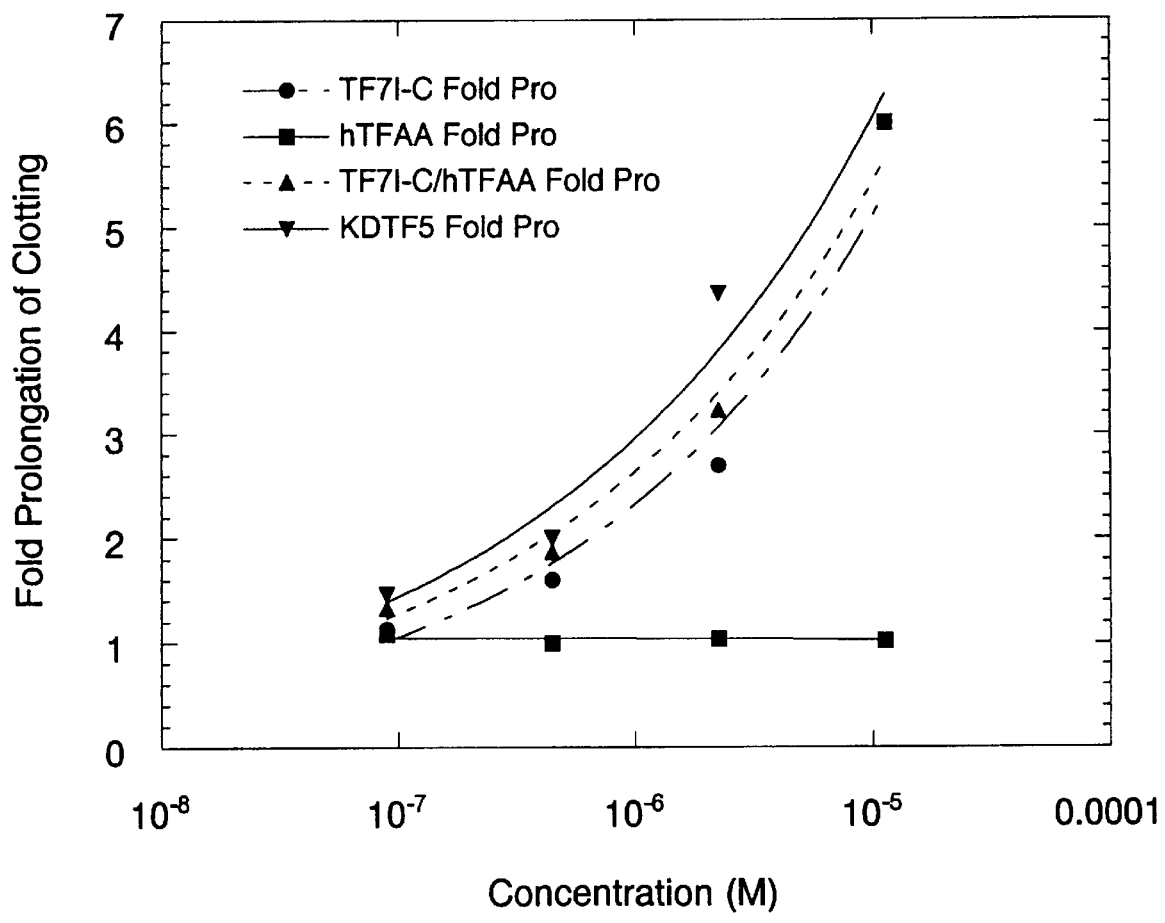
FIG. 8 depicts the effects of TF-FVIIa inhibitors on the clotting time determined in an activated partial thromboplastin time (APTT) assay. The sample (citrated human plasma and inhibitor) and activator (Intrumentation Laboratories Cephalin+Activator APTT Reagent) were incubated together for 70 seconds at 37° C., then $CaCl_2$ was added and the clotting time was determined. Fold prolongation of clotting time was defined as the clotting time in the presence of the indicated concentration of inhibitor divided by the clotting time in the absence of inhibitor. This latter time was 63.7±9.0 seconds. Data are shown for KDTF5 (▼), TF7I-C (●), hTFAA (■), and equimolar mixture of TF7I-C and hTFAA (▲).

The fusion protein KDTF5 gave a very potent inhibition of clotting in the PT assay as shown in FIG. 7. KDTF5 was more potent than TF7I-C or hTFAA alone and also inhibited at a lower dose than observed for a mixture of TF7I-C and hTFAA. With KDTF5 a 2-fold prolongation in clotting time was obtained at an inhibitor concentration of about 800 nM. A 2-fold prolongation in clotting time was obtained at 1.9 $\mu$M for the equimolar mixture of TF7I-C and hTFAA. A concentration of 4 $\mu$M hTFAA alone gave a 2-fold increase in clotting time whereas a 2-fold prolongation was not obtained with TF7I-C at the highest concentration tested. These data show that KDTF5 is a potent inhibitor of TF dependent clotting and has greater potency than the noncovalent mixture of the two inhibitors. As shown in FIG. 8, KDTF5 retained the effect on clotting time in an APTT assay previously observed for TF7I-C alone (Dennis, M. S. & Lazarus, R. A. J. Biol. Chem. 269: 22129–22136 [1994]). Both KDTF5 and the noncovalent mixture of TF7I-C and hTFAA were slightly more potent that TF7I-C alone in inhibiting the intrinsic pathway of blood coagulation. An inhibitor concentration of about 200 nM for either KDTF5 or the TF7I-C/hTFAA mixture gave a 2-fold prolongation in clotting time. A TF7I-C concentration of 400 nM was required to give a 2-fold prolongation in clotting time. At the concentrations tested, hTFAA alone had no effect on the clotting time determined in an APTT assay.

Example 6

Determination of antithrombotic potential in a rabbit model of deep medial injury Male New Zealand white rabbits (~4 kg) are anesthetized to surgical anesthesia plane with an IM injection of Ketamine/Xylaxine. The rabbits are placed supine on a restraining board, warmed to 37° C., and the neck and inner thigh area shaved. Teflon catheters are placed in a marginal ear vein and femoral artery for drug delivery and sample collection respectively. Prior to treatment, blood samples are collected for coagulation tests (APTT and PT). Bleeding time is assessed from a cut made in the cuticle portion of a hind limb nail. Incisions are made in the neck region and the entire left common carotid artery and its branches are surgically isolated. An ultrasonic flow probe (Transonics®) is placed on the common carotid approximately 5 cm caudal to the common—internal bifurcation. After blood flow reaches a stable baseline, drugs (saline or test compounds) are delivered via the marginal ear vein. A deflated embolectomy catheter (Fogarty®, 3F) was then introduced into the lumen of the common carotid via an incision in the lingual branch. Blood flow through the artery is stopped briefly while the catheter is introduced and loosely secured with 2–0 silk tie at the incision site. After the catheter is in place and secure, blood flow is restored. The deflated balloon is advanced to within 2 mm of the flow probe and inflated with saline until resistance of the vessel wall is felt. The catheter is pulled back with a steady motion to the first branch and then deflated.

This procedure is repeated several times for each experimental animal, after which the catheter is removed. The ballooning procedure, from first insertion to removal of the catheter takes approximately 3 to 5 minutes and results in an area of damage that is 1.5 to 2 cm in length. Over 40 minutes, blood samples are taken for PT measurements, cuticle bleeding times are assessed and blood flow through the carotid monitored. Duration of patency is defined as the total amount of time (maximum=40 minutes) that any measurable blood flow is detected in the artery. Patency rate refers to the percentage of animals tested who had carotid artery blood flow≧5 minutes.

At the end of the experiment, the rabbit is euthanized and the carotid artery removed and opened. If any thrombus is present, it is removed, blotted and the weight recorded.

What is claimed is:

1. A method for inhibiting human tissue factor-Factor VIIa (TF-FVIIa) procoagulant activity in a mammal comprising administering a therapeutically effective amount of a pharmaceutical composition comprising a pharmaceutically acceptable excipient and a fusion protein comprising:

a) a Factor VIIa ("FVIIa") active site inhibitor domain;

b) a linker domain; and c) a tissue factor ("TF") domain to the mammal.

2. The method of claim 1 further comprising administrating the composition in combination with a thrombolytic agent.

3. The method of claim 1 further comprising administrating the composition in combination with an anticoagulant.

4. A method of treating a mammal for which inhibiting Factor VIIa is indicated comprising administering a pharmaceutically effective amount of a pharmaceutical composition comprising a pharmaceutically acceptable excipient and a fusion protein comprising:

a) a Factor VIIa ("FVIIa") active site inhibitor domain;

b) a linker domain; and c) a tissue factor ("TF") domain to the mammal.

* * * * *

SEQUENCE LISTING ( 1 ) GENERAL INFORMATION:

( i i i ) NUMBER OF SEQUENCES: 58

( 2 ) INFORMATION FOR SEQ ID NO:1:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:1:

```
Val  Arg  Glu  Val  Cys  Ser  Glu  Gln  Ala  Glu
 1                  5                         10
```

( 2 ) INFORMATION FOR SEQ ID NO:2:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:2:

```
Met  His  Ser  Phe  Cys  Ala  Phe  Lys  Ala  Asp
 1                  5                         10
```

( 2 ) INFORMATION FOR SEQ ID NO:3:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:3:

```
Lys  Pro  Asp  Phe  Cys  Phe  Leu  Glu  Glu  Asp
 1                  5                         10
```

( 2 ) INFORMATION FOR SEQ ID NO:4:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:4:

```
Gly  Pro  Ser  Trp  Cys  Leu  Thr  Pro  Ala  Asp
 1                  5                         10
```

( 2 ) INFORMATION FOR SEQ ID NO:5:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:5:

```
Lys  Glu  Asp  Ser  Cys  Gln  Leu  Gly  Tyr  Ser
 1                  5                         10
```

( 2 ) INFORMATION FOR SEQ ID NO:6:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:6:

```
Thr  Val  Ala  Ala  Cys  Asn  Leu  Pro  Ile  Val
 1                  5                         10
```

( 2 ) INFORMATION FOR SEQ ID NO:7:

( i ) SEQUENCE CHARACTERISTICS:
  ( A ) LENGTH: 10 amino acids
  ( B ) TYPE: Amino Acid
  ( D ) TOPOLOGY: Linear ( x i ) SEQUENCE DESCRIPTION: SEQ ID NO:7:

Leu Pro Asn Val Cys Ala Phe Pro Met Glu
 1               5                  10

( 2 ) INFORMATION FOR SEQ ID NO:8:

( i ) SEQUENCE CHARACTERISTICS:
  ( A ) LENGTH: 10 amino acids
  ( B ) TYPE: Amino Acid
  ( D ) TOPOLOGY: Linear ( x i ) SEQUENCE DESCRIPTION: SEQ ID NO:8:

Arg Pro Asp Phe Cys Leu Glu Pro Pro Tyr
 1               5                  10

( 2 ) INFORMATION FOR SEQ ID NO:9:

( i ) SEQUENCE CHARACTERISTICS:
  ( A ) LENGTH: 14 amino acids
  ( B ) TYPE: Amino Acid
  ( D ) TOPOLOGY: Linear ( x i ) SEQUENCE DESCRIPTION: SEQ ID NO:9:

Arg Trp Tyr Phe Asp Val Thr Glu Gly Lys Cys Ala Pro Phe
 1               5                  10                 14

( 2 ) INFORMATION FOR SEQ ID NO:10:

( i ) SEQUENCE CHARACTERISTICS:
  ( A ) LENGTH: 14 amino acids
  ( B ) TYPE: Amino Acid
  ( D ) TOPOLOGY: Linear ( x i ) SEQUENCE DESCRIPTION: SEQ ID NO:10:

Arg Phe Phe Phe Asn Ile Phe Thr Arg Gln Cys Glu Glu Phe
 1               5                  10                 14

( 2 ) INFORMATION FOR SEQ ID NO:11:

( i ) SEQUENCE CHARACTERISTICS:
  ( A ) LENGTH: 14 amino acids
  ( B ) TYPE: Amino Acid
  ( D ) TOPOLOGY: Linear ( x i ) SEQUENCE DESCRIPTION: SEQ ID NO:11:

Arg Tyr Phe Tyr Asn Asn Gln Thr Lys Gln Cys Glu Arg Phe
 1               5                  10                 14

( 2 ) INFORMATION FOR SEQ ID NO:12:

( i ) SEQUENCE CHARACTERISTICS:
  ( A ) LENGTH: 14 amino acids
  ( B ) TYPE: Amino Acid
  ( D ) TOPOLOGY: Linear ( x i ) SEQUENCE DESCRIPTION: SEQ ID NO:12:

Arg Phe Tyr Tyr Asn Ser Val Ile Gly Lys Cys Arg Pro Phe
 1               5                  10                 14

( 2 ) INFORMATION FOR SEQ ID NO:13:

( i ) SEQUENCE CHARACTERISTICS:

(A) LENGTH: 14 amino acids
(B) TYPE: Amino Acid
(D) TOPOLOGY: Linear (xi) SEQUENCE DESCRIPTION: SEQ ID NO:13:

Arg Tyr Phe Tyr Asn Gly Thr Ser Met Ala Cys Glu Thr Phe
 1               5                  10                14

(2) INFORMATION FOR SEQ ID NO:14:

(i) SEQUENCE CHARACTERISTICS:
(A) LENGTH: 14 amino acids
(B) TYPE: Amino Acid
(D) TOPOLOGY: Linear (xi) SEQUENCE DESCRIPTION: SEQ ID NO:14:

Leu Trp Ala Phe Asp Ala Val Lys Gly Lys Cys Val Leu Phe
 1               5                  10                14

(2) INFORMATION FOR SEQ ID NO:15:

(i) SEQUENCE CHARACTERISTICS:
(A) LENGTH: 14 amino acids
(B) TYPE: Amino Acid
(D) TOPOLOGY: Linear (xi) SEQUENCE DESCRIPTION: SEQ ID NO:15:

Lys Trp Tyr Tyr Asp Pro Asn Thr Lys Ser Cys Ala Arg Phe
 1               5                  10                14

(2) INFORMATION FOR SEQ ID NO:16:

(i) SEQUENCE CHARACTERISTICS:
(A) LENGTH: 14 amino acids
(B) TYPE: Amino Acid
(D) TOPOLOGY: Linear (xi) SEQUENCE DESCRIPTION: SEQ ID NO:16:

Arg Trp Phe Phe Asn Phe Glu Thr Gly Glu Cys Glu Leu Phe
 1               5                  10                14

(2) INFORMATION FOR SEQ ID NO:17:

(i) SEQUENCE CHARACTERISTICS:
(A) LENGTH: 14 amino acids
(B) TYPE: Amino Acid
(D) TOPOLOGY: Linear (xi) SEQUENCE DESCRIPTION: SEQ ID NO:17:

Arg Tyr Phe Tyr Asn Ala Lys Ala Gly Leu Cys Gln Thr Phe
 1               5                  10                14

(2) INFORMATION FOR SEQ ID NO:18:

(i) SEQUENCE CHARACTERISTICS:
(A) LENGTH: 19 amino acids
(B) TYPE: Amino Acid
(D) TOPOLOGY: Linear (xi) SEQUENCE DESCRIPTION: SEQ ID NO:18:

Gly Asn Arg Asn Asn Phe Asp Thr Glu Glu Tyr Cys Ala Ala Val
 1               5                  10                    15

Cys Gly Ser Ala
              19

(2) INFORMATION FOR SEQ ID NO:19:

(i) SEQUENCE CHARACTERISTICS:
(A) LENGTH: 19 amino acids
(B) TYPE: Amino Acid
(D) TOPOLOGY: Linear (xi) SEQUENCE DESCRIPTION: SEQ ID NO:19:

Gly Asn Arg Asn Asn Phe Asp Thr Glu Glu Tyr Cys Met Ala Val
 1               5                  10                  15
Cys Gly Ser Ala
         19

(2) INFORMATION FOR SEQ ID NO:20:

(i) SEQUENCE CHARACTERISTICS:
(A) LENGTH: 19 amino acids
(B) TYPE: Amino Acid
(D) TOPOLOGY: Linear (xi) SEQUENCE DESCRIPTION: SEQ ID NO:20:

Gly Asn Gln Asn Arg Phe Glu Ser Leu Glu Glu Cys Lys Lys Met
 1               5                  10                  15
Cys Thr Arg Asp
         19

(2) INFORMATION FOR SEQ ID NO:21:

(i) SEQUENCE CHARACTERISTICS:
(A) LENGTH: 19 amino acids
(B) TYPE: Amino Acid
(D) TOPOLOGY: Linear (xi) SEQUENCE DESCRIPTION: SEQ ID NO:21:

Gly Asn Met Asn Asn Phe Glu Thr Leu Glu Glu Cys Lys Asn Ile
 1               5                  10                  15
Cys Glu Asp Gly
         19

(2) INFORMATION FOR SEQ ID NO:22:

(i) SEQUENCE CHARACTERISTICS:
(A) LENGTH: 19 amino acids
(B) TYPE: Amino Acid
(D) TOPOLOGY: Linear (xi) SEQUENCE DESCRIPTION: SEQ ID NO:22:

Gly Asn Glu Asn Asn Phe Thr Ser Lys Gln Glu Cys Leu Arg Ala
 1               5                  10                  15
Cys Lys Lys Gly
         19

(2) INFORMATION FOR SEQ ID NO:23:

(i) SEQUENCE CHARACTERISTICS:
(A) LENGTH: 19 amino acids
(B) TYPE: Amino Acid
(D) TOPOLOGY: Linear (xi) SEQUENCE DESCRIPTION: SEQ ID NO:23:

Gly Asn Gly Asn Asn Phe Val Thr Glu Lys Glu Cys Leu Gln Thr
 1               5                  10                  15
Cys Arg Thr Val
         19

(2) INFORMATION FOR SEQ ID NO:24:

( i ) SEQUENCE CHARACTERISTICS:
( A ) LENGTH: 19 amino acids
( B ) TYPE: Amino Acid
( D ) TOPOLOGY: Linear ( x i ) SEQUENCE DESCRIPTION: SEQ ID NO:24:

Gly Asn Gly Asn Lys Phe Tyr Ser Glu Lys Glu Cys Arg Glu Tyr
1               5                   10                  15
Cys Gly Val Pro
            19

( 2 ) INFORMATION FOR SEQ ID NO:25:

( i ) SEQUENCE CHARACTERISTICS:
( A ) LENGTH: 19 amino acids
( B ) TYPE: Amino Acid
( D ) TOPOLOGY: Linear ( x i ) SEQUENCE DESCRIPTION: SEQ ID NO:25:

Gly Asn Glu Asn Lys Phe Gly Ser Gln Lys Glu Cys Glu Lys Val
1               5                   10                  15
Cys Ala Pro Val
            19

( 2 ) INFORMATION FOR SEQ ID NO:26:

( i ) SEQUENCE CHARACTERISTICS:
( A ) LENGTH: 19 amino acids
( B ) TYPE: Amino Acid
( D ) TOPOLOGY: Linear ( x i ) SEQUENCE DESCRIPTION: SEQ ID NO:26:

Gly Asn Ser Asn Asn Phe Leu Arg Lys Glu Lys Cys Glu Lys Phe
1               5                   10                  15
Cys Lys Phe Thr
            19

( 2 ) INFORMATION FOR SEQ ID NO:27:

( i ) SEQUENCE CHARACTERISTICS:
( A ) LENGTH: 19 amino acids
( B ) TYPE: Amino Acid
( D ) TOPOLOGY: Linear ( x i ) SEQUENCE DESCRIPTION: SEQ ID NO:27:

Ala Lys Arg Asn Asn Phe Lys Ser Ala Glu Asp Cys Met Arg Thr
1               5                   10                  15
Cys Gly Gly Ala
            19

( 2 ) INFORMATION FOR SEQ ID NO:28:

( i ) SEQUENCE CHARACTERISTICS:
( A ) LENGTH: 58 amino acids
( B ) TYPE: Amino Acid
( D ) TOPOLOGY: Linear ( x i ) SEQUENCE DESCRIPTION: SEQ ID NO:28:

Val Arg Glu Val Cys Ser Glu Gln Ala Glu Pro Gly Val Cys Arg
1               5                   10                  15
Ala Leu Ile Leu Arg Trp Tyr Phe Asp Val Thr Glu Gly Lys Cys
                20                  25                  30
Ala Pro Phe Phe Tyr Gly Gly Cys Gly Gly Asn Arg Asn Asn Phe
                35                  40                  45

| Asp | Thr | Glu | Glu | Tyr | Cys | Ala | Ala | Val | Cys | Gly | Ser | Ala |
|     |     |     |     | 50  |     |     |     |     | 55  |     |     | 58  |

( 2 ) INFORMATION FOR SEQ ID NO:29:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:29:

| Val | Arg | Glu | Val | Cys | Ser | Glu | Gln | Ala | Glu | Pro | Gly | Trp | Cys | Arg |
| 1   |     |     |     | 5   |     |     |     |     | 10  |     |     |     |     | 15  |

| Ala | Leu | Ile | Leu | Arg | Trp | Tyr | Phe | Asp | Val | Thr | Glu | Gly | Lys | Cys |
|     |     |     |     | 20  |     |     |     |     | 25  |     |     |     |     | 30  |

| Ala | Pro | Phe | Phe | Tyr | Gly | Gly | Cys | Gly | Gly | Asn | Arg | Asn | Asn | Phe |
|     |     |     |     | 35  |     |     |     |     | 40  |     |     |     |     | 45  |

| Asp | Thr | Glu | Glu | Tyr | Cys | Ala | Ala | Val | Cys | Gly | Ser | Ala |
|     |     |     |     | 50  |     |     |     |     | 55  |     |     | 58  |

( 2 ) INFORMATION FOR SEQ ID NO:30:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:30:

| Val | Arg | Glu | Val | Cys | Ser | Glu | Gln | Ala | Glu | Pro | Gly | Phe | Cys | Arg |
| 1   |     |     |     | 5   |     |     |     |     | 10  |     |     |     |     | 15  |

| Ala | Leu | Ile | Leu | Arg | Trp | Tyr | Phe | Asp | Val | Thr | Glu | Gly | Lys | Cys |
|     |     |     |     | 20  |     |     |     |     | 25  |     |     |     |     | 30  |

| Ala | Pro | Phe | Phe | Tyr | Gly | Gly | Cys | Gly | Gly | Asn | Arg | Asn | Asn | Phe |
|     |     |     |     | 35  |     |     |     |     | 40  |     |     |     |     | 45  |

| Asp | Thr | Glu | Glu | Tyr | Cys | Ala | Ala | Val | Cys | Gly | Ser | Ala |
|     |     |     |     | 50  |     |     |     |     | 55  |     |     | 58  |

( 2 ) INFORMATION FOR SEQ ID NO:31:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:31:

| Val | Arg | Glu | Val | Cys | Ser | Glu | Gln | Ala | Glu | Gly | Gly | Trp | Cys | Arg |
| 1   |     |     |     | 5   |     |     |     |     | 10  |     |     |     |     | 15  |

| Ala | Leu | Ile | Leu | Arg | Trp | Tyr | Phe | Asp | Val | Thr | Glu | Gly | Lys | Cys |
|     |     |     |     | 20  |     |     |     |     | 25  |     |     |     |     | 30  |

| Ala | Pro | Phe | Phe | Tyr | Gly | Gly | Cys | Gly | Gly | Asn | Arg | Asn | Asn | Phe |
|     |     |     |     | 35  |     |     |     |     | 40  |     |     |     |     | 45  |

| Asp | Thr | Glu | Glu | Tyr | Cys | Ala | Ala | Val | Cys | Gly | Ser | Ala |
|     |     |     |     | 50  |     |     |     |     | 55  |     |     | 58  |

( 2 ) INFORMATION FOR SEQ ID NO:32:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:32:

| Val | Arg | Glu | Val | Cys | Ser | Glu | Gln | Ala | Glu | Pro | Gly | Pro | Cys | Arg |

|   1 |   |   |   |   5 |   |   |   |   |  10 |   |   |   |   |  15 |
|---|---|---|---|---|---|---|---|---|---|---|---|---|---|---|
| Ala | Met | Ile | Ser | Arg | Trp | Tyr | Phe | Asp | Val | Thr | Glu | Gly | Lys | Cys |
|   |   |   |   |  20 |   |   |   |   |  25 |   |   |   |   |  30 |
| Ala | Pro | Phe | Phe | Tyr | Gly | Gly | Cys | Tyr | Gly | Asn | Arg | Asn | Asn | Phe |
|   |   |   |   |  35 |   |   |   |   |  40 |   |   |   |   |  45 |
| Asp | Thr | Glu | Glu | Tyr | Cys | Ala | Ala | Val | Cys | Gly | Ser | Ala |   |   |
|   |   |   |   |  50 |   |   |   |   |  55 |   |   |  58 |   |   |

(2) INFORMATION FOR SEQ ID NO:33:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:33:

| Val | Arg | Glu | Val | Cys | Ser | Glu | Gln | Ala | Glu | Pro | Gly | Trp | Cys | Arg |
|---|---|---|---|---|---|---|---|---|---|---|---|---|---|---|
|   1 |   |   |   |   5 |   |   |   |   |  10 |   |   |   |   |  15 |
| Ala | Met | Ile | Ser | Arg | Trp | Tyr | Phe | Asp | Val | Thr | Glu | Gly | Lys | Cys |
|   |   |   |   |  20 |   |   |   |   |  25 |   |   |   |   |  30 |
| Ala | Pro | Phe | Ile | Tyr | Gly | Gly | Cys | Gly | Gly | Asn | Arg | Asn | Asn | Phe |
|   |   |   |   |  35 |   |   |   |   |  40 |   |   |   |   |  45 |
| Asp | Thr | Glu | Glu | Tyr | Cys | Ala | Ala | Val | Cys | Gly | Ser | Ala |   |   |
|   |   |   |   |  50 |   |   |   |   |  55 |   |   |  58 |   |   |

(2) INFORMATION FOR SEQ ID NO:34:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:34:

| Val | Arg | Glu | Val | Cys | Ser | Glu | Gln | Ala | Glu | Pro | Gly | Pro | Cys | Lys |
|---|---|---|---|---|---|---|---|---|---|---|---|---|---|---|
|   1 |   |   |   |   5 |   |   |   |   |  10 |   |   |   |   |  15 |
| Ala | Met | Ile | Ser | Arg | Trp | Tyr | Phe | Asp | Val | Thr | Glu | Gly | Lys | Cys |
|   |   |   |   |  20 |   |   |   |   |  25 |   |   |   |   |  30 |
| Ala | Pro | Phe | Ile | Tyr | Gly | Gly | Cys | Trp | Gly | Asn | Arg | Asn | Asn | Phe |
|   |   |   |   |  35 |   |   |   |   |  40 |   |   |   |   |  45 |
| Asp | Thr | Glu | Glu | Tyr | Cys | Ala | Ala | Val | Cys | Gly | Ser | Ala |   |   |
|   |   |   |   |  50 |   |   |   |   |  55 |   |   |  58 |   |   |

(2) INFORMATION FOR SEQ ID NO:35:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:35:

| Val | Arg | Glu | Val | Cys | Ser | Glu | Gln | Ala | Glu | Thr | Gly | Pro | Cys | Arg |
|---|---|---|---|---|---|---|---|---|---|---|---|---|---|---|
|   1 |   |   |   |   5 |   |   |   |   |  10 |   |   |   |   |  15 |
| Ala | Leu | Ile | Ser | Arg | Trp | Tyr | Phe | Asp | Val | Thr | Glu | Gly | Lys | Cys |
|   |   |   |   |  20 |   |   |   |   |  25 |   |   |   |   |  30 |
| Ala | Pro | Phe | Trp | Tyr | Gly | Gly | Cys | Gly | Gly | Asn | Arg | Asn | Asn | Phe |
|   |   |   |   |  35 |   |   |   |   |  40 |   |   |   |   |  45 |
| Asp | Thr | Glu | Glu | Tyr | Cys | Ala | Ala | Val | Cys | Gly | Ser | Ala |   |   |
|   |   |   |   |  50 |   |   |   |   |  55 |   |   |  58 |   |   |

(2) INFORMATION FOR SEQ ID NO:36:

( i ) SEQUENCE CHARACTERISTICS:
 ( A ) LENGTH: 58 amino acids
 ( B ) TYPE: Amino Acid
 ( D ) TOPOLOGY: Linear ( x i ) SEQUENCE DESCRIPTION: SEQ ID NO:36:

```
Val Arg Glu Val Cys Ser Glu Gln Ala Glu Thr Gly Pro Cys Arg
 1               5                  10                  15

Ala Leu Ile Ser Arg Trp Tyr Phe Asp Val Thr Glu Gly Lys Cys
                20                  25                  30

Ala Pro Phe Tyr Tyr Gly Gly Cys Gly Gly Asn Arg Asn Asn Phe
                35                  40                  45

Asp Thr Glu Glu Tyr Cys Ala Ala Val Cys Gly Ser Ala
                50                  55          58
```

( 2 ) INFORMATION FOR SEQ ID NO:37:

( i ) SEQUENCE CHARACTERISTICS:
  ( A ) LENGTH: 58 amino acids
  ( B ) TYPE: Amino Acid
  ( D ) TOPOLOGY: Linear ( x i ) SEQUENCE DESCRIPTION: SEQ ID NO:37:

```
Val Arg Glu Val Cys Ser Glu Gln Ala Glu Pro Gly Val Cys Arg
 1               5                  10                  15

Ala Leu Ile Leu Arg Trp Tyr Phe Asp Val Thr Glu Gly Lys Cys
                20                  25                  30

Ala Pro Phe Phe Tyr Gly Gly Cys Tyr Gly Asn Arg Asn Asn Phe
                35                  40                  45

Asp Thr Glu Glu Tyr Cys Ala Ala Val Cys Gly Ser Ala
                50                  55          58
```

( 2 ) INFORMATION FOR SEQ ID NO:38:

( i ) SEQUENCE CHARACTERISTICS:
  ( A ) LENGTH: 58 amino acids
  ( B ) TYPE: Amino Acid
  ( D ) TOPOLOGY: Linear ( x i ) SEQUENCE DESCRIPTION: SEQ ID NO:38:

```
Val Arg Glu Val Cys Ser Glu Gln Ala Glu Pro Gly Leu Cys Arg
 1               5                  10                  15

Ala Leu Ile Ser Arg Trp Tyr Phe Asp Val Thr Glu Gly Lys Cys
                20                  25                  30

Ala Pro Phe Phe Tyr Gly Gly Cys Tyr Gly Asn Arg Asn Asn Phe
                35                  40                  45

Asp Thr Glu Glu Tyr Cys Ala Ala Val Cys Gly Ser Ala
                50                  55          58
```

( 2 ) INFORMATION FOR SEQ ID NO:39:

( i ) SEQUENCE CHARACTERISTICS:
  ( A ) LENGTH: 58 amino acids
  ( B ) TYPE: Amino Acid
  ( D ) TOPOLOGY: Linear ( x i ) SEQUENCE DESCRIPTION: SEQ ID NO:39:

```
Val Arg Glu Val Cys Ser Glu Gln Ala Glu Pro Gly Trp Cys Arg
 1               5                  10                  15

Ala Leu Ile Leu Arg Trp Tyr Phe Asp Val Thr Glu Gly Lys Cys
                20                  25                  30

Ala Pro Phe Phe Tyr Gly Gly Cys Tyr Gly Asn Arg Asn Asn Phe
```

Asp Thr Glu Glu Tyr Cys Ala Ala Val Cys Gly Ser Ala
                50                      55              58

( 2 ) INFORMATION FOR SEQ ID NO:40:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:40:

Val Arg Glu Val Cys Ser Glu Gln Ala Glu Pro Gly Pro Cys Arg
 1               5                      10                      15

Ala Leu Ile Leu Arg Trp Tyr Phe Asp Val Thr Glu Gly Lys Cys
                20                      25                      30

Ala Pro Phe Phe Tyr Gly Gly Cys Gly Gly Asn Arg Asn Asn Phe
                35                      40                      45

Asp Thr Glu Glu Tyr Cys Ala Ala Val Cys Gly Ser Ala
                50                      55              58

( 2 ) INFORMATION FOR SEQ ID NO:41:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:41:

Val Arg Glu Val Cys Ser Glu Gln Ala Glu Pro Gly Pro Cys Arg
 1               5                      10                      15

Ala Met Met Lys Arg Trp Tyr Phe Asp Val Thr Glu Gly Lys Cys
                20                      25                      30

Ala Pro Phe Ile Tyr Gly Gly Cys His Gly Asn Arg Asn Asn Phe
                35                      40                      45

Asp Thr Glu Glu Tyr Cys Ala Ala Val Cys Gly Ser Ala
                50                      55              58

( 2 ) INFORMATION FOR SEQ ID NO:42:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:42:

Val Arg Glu Val Cys Ser Glu Gln Ala Glu Pro Gly Pro Cys Arg
 1               5                      10                      15

Ala Leu Met Lys Arg Trp Tyr Phe Asp Val Thr Glu Gly Lys Cys
                20                      25                      30

Ala Pro Phe Val Tyr Gly Gly Cys Tyr Gly Asn Arg Asn Asn Phe
                35                      40                      45

Asp Thr Glu Glu Tyr Cys Ala Ala Val Cys Gly Ser Ala
                50                      55              58

( 2 ) INFORMATION FOR SEQ ID NO:43:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:43:

Val Arg Glu Val Cys Ser Glu Gln Ala Glu Pro Gly Pro Cys Arg
1               5                       10                      15

Ala Leu Met Lys Arg Trp Tyr Phe Asp Val Thr Glu Gly Lys Cys
                20                      25                      30

Ala Pro Phe Val Tyr Gly Gly Cys Phe Gly Asn Arg Asn Asn Phe
                35                      40                      45

Asp Thr Glu Glu Tyr Cys Ala Ala Val Cys Gly Ser Ala
                50                      55              58

( 2 ) INFORMATION FOR SEQ ID NO:44:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:44:

Val Arg Glu Val Cys Ser Glu Gln Ala Glu Pro Gly Pro Cys Arg
1               5                       10                      15

Ala Leu Met Lys Arg Trp Tyr Phe Asp Val Thr Glu Gly Lys Cys
                20                      25                      30

Ala Pro Phe Ile Tyr Gly Gly Cys Tyr Gly Asn Arg Asn Asn Phe
                35                      40                      45

Asp Thr Glu Glu Tyr Cys Ala Ala Val Cys Gly Ser Ala
                50                      55              58

( 2 ) INFORMATION FOR SEQ ID NO:45:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:45:

Val Arg Glu Val Cys Ser Glu Gln Ala Glu Pro Gly Pro Cys Arg
1               5                       10                      15

Ala Met Tyr Lys Arg Trp Tyr Phe Asp Val Thr Glu Gly Lys Cys
                20                      25                      30

Ala Pro Phe Ile Tyr Gly Gly Cys Tyr Gly Asn Arg Asn Asn Phe
                35                      40                      45

Asp Thr Glu Glu Tyr Cys Ala Ala Val Cys Gly Ser Ala
                50                      55              58

( 2 ) INFORMATION FOR SEQ ID NO:46:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:46:

Val Arg Glu Val Cys Ser Glu Gln Ala Glu Pro Gly Val Cys Arg
1               5                       10                      15

Ala Met Met Lys Arg Trp Tyr Phe Asp Val Thr Glu Gly Lys Cys
                20                      25                      30

Ala Pro Phe Ile Tyr Gly Gly Cys Gly Gly Asn Arg Asn Asn Phe
                35                      40                      45

Asp Thr Glu Glu Tyr Cys Ala Ala Val Cys Gly Ser Ala
                50                      55              58

( 2 ) INFORMATION FOR SEQ ID NO:47:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:47:

```
Val Arg Glu Val Cys Ser Glu Gln Ala Glu Pro Gly Pro Cys Lys
 1               5                  10                  15
Ala Leu Met Arg Arg Trp Tyr Phe Asp Val Thr Glu Gly Lys Cys
                20                  25                  30
Ala Pro Phe Tyr Tyr Gly Gly Cys Tyr Gly Asn Arg Asn Asn Phe
                35                  40                  45
Asp Thr Glu Glu Tyr Cys Ala Ala Val Cys Gly Ser Ala
                50                  55          58
```

( 2 ) INFORMATION FOR SEQ ID NO:48:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:48:

```
Val Arg Glu Val Cys Ser Glu Gln Ala Glu Pro Gly Pro Cys Lys
 1               5                  10                  15
Ala Ile Met Lys Arg Trp Tyr Phe Asp Val Thr Glu Gly Lys Cys
                20                  25                  30
Ala Pro Phe Ile Tyr Gly Gly Cys His Gly Asn Arg Asn Asn Phe
                35                  40                  45
Asp Thr Glu Glu Tyr Cys Ala Ala Val Cys Gly Ser Ala
                50                  55          58
```

( 2 ) INFORMATION FOR SEQ ID NO:49:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:49:

```
Val Arg Glu Val Cys Ser Glu Gln Ala Glu Pro Gly Pro Cys Lys
 1               5                  10                  15
Ala Leu Met Lys Arg Trp Tyr Phe Asp Val Thr Glu Gly Lys Cys
                20                  25                  30
Ala Pro Phe Tyr Tyr Gly Gly Cys His Gly Asn Arg Asn Asn Phe
                35                  40                  45
Asp Thr Glu Glu Tyr Cys Ala Ala Val Cys Gly Ser Ala
                50                  55          58
```

( 2 ) INFORMATION FOR SEQ ID NO:50:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:50:

```
Val Arg Glu Val Cys Ser Glu Gln Ala Glu Pro Gly Pro Cys Lys
 1               5                  10                  15
Ala Leu Met Lys Arg Trp Tyr Phe Asp Val Thr Glu Gly Lys Cys
                20                  25                  30
```

```
Ala Pro Phe Trp Tyr Gly Gly Cys Trp Gly Asn Arg Asn Asn Phe
             35                      40                      45

Asp Thr Glu Glu Tyr Cys Ala Ala Val Cys Gly Ser Ala
             50                      55              58
```

( 2 ) INFORMATION FOR SEQ ID NO:51:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:51:

```
Val Arg Glu Val Cys Ser Glu Gln Ala Glu Pro Gly Pro Cys Lys
1                5                      10                      15

Ala Met Ile Lys Arg Trp Tyr Phe Asp Val Thr Glu Gly Lys Cys
             20                      25                      30

Ala Pro Phe Leu Tyr Gly Gly Cys Tyr Gly Asn Arg Asn Asn Phe
             35                      40                      45

Asp Thr Glu Glu Tyr Cys Ala Ala Val Cys Gly Ser Ala
             50                      55              58
```

( 2 ) INFORMATION FOR SEQ ID NO:52:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:52:

```
Val Arg Glu Val Cys Ser Glu Gln Ala Glu Pro Gly Pro Cys Lys
1                5                      10                      15

Ala Leu Met Lys Arg Trp Tyr Phe Asp Val Thr Glu Gly Lys Cys
             20                      25                      30

Ala Pro Phe Phe Tyr Gly Gly Cys Tyr Gly Asn Arg Asn Asn Phe
             35                      40                      45

Asp Thr Glu Glu Tyr Cys Ala Ala Val Cys Gly Ser Ala
             50                      55              58
```

( 2 ) INFORMATION FOR SEQ ID NO:53:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:53:

```
Val Arg Glu Val Cys Ser Glu Gln Ala Glu Pro Gly Pro Cys Lys
1                5                      10                      15

Ala Leu Met Lys Arg Trp Tyr Phe Asp Val Thr Glu Gly Lys Cys
             20                      25                      30

Ala Pro Phe Tyr Tyr Gly Gly Cys Tyr Gly Asn Arg Asn Asn Phe
             35                      40                      45

Asp Thr Glu Glu Tyr Cys Ala Ala Val Cys Gly Ser Ala
             50                      55              58
```

( 2 ) INFORMATION FOR SEQ ID NO:54:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:54:

| Val | Arg | Glu | Val | Cys | Ser | Gln | Ala | Glu | Pro | Gly | Pro | Cys | Lys |
| 1 | | | | 5 | | | | | 10 | | | | 15 |

| Ala | Leu | Met | Lys | Arg | Trp | Tyr | Phe | Asp | Val | Thr | Glu | Gly | Lys | Cys |
| | | | | 20 | | | | | 25 | | | | | 30 |

| Ala | Pro | Phe | Val | Tyr | Gly | Gly | Cys | Tyr | Gly | Asn | Arg | Asn | Asn | Phe |
| | | | | 35 | | | | | 40 | | | | | 45 |

| Asp | Thr | Glu | Glu | Tyr | Cys | Ala | Ala | Val | Cys | Gly | Ser | Ala |
| | | | | 50 | | | | | 55 | | | 58 |

( 2 ) INFORMATION FOR SEQ ID NO:55:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:55:

| Val | Arg | Glu | Val | Cys | Ser | Gln | Ala | Glu | Pro | Gly | Ala | Cys | Lys |
| 1 | | | | 5 | | | | | 10 | | | | 15 |

| Ala | Met | Tyr | Lys | Arg | Trp | Tyr | Phe | Asp | Val | Thr | Glu | Gly | Lys | Cys |
| | | | | 20 | | | | | 25 | | | | | 30 |

| Ala | Pro | Phe | Ile | Tyr | Gly | Gly | Cys | Gly | Gly | Asn | Arg | Asn | Asn | Phe |
| | | | | 35 | | | | | 40 | | | | | 45 |

| Asp | Thr | Glu | Glu | Tyr | Cys | Ala | Ala | Val | Cys | Gly | Ser | Ala |
| | | | | 50 | | | | | 55 | | | 58 |

( 2 ) INFORMATION FOR SEQ ID NO:56:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:56:

| Val | Arg | Glu | Val | Cys | Ser | Gln | Ala | Glu | Pro | Gly | Pro | Gly | Arg |
| 1 | | | | 5 | | | | | 10 | | | | 15 |

| Ala | Leu | Ile | Leu | Arg | Trp | Tyr | Phe | Asp | Val | Thr | Glu | Gly | Lys | Cys |
| | | | | 20 | | | | | 25 | | | | | 30 |

| Ala | Pro | Phe | Phe | Tyr | Gly | Gly | Ala | Tyr | Gly | Asn | Arg | Asn | Asn | Phe |
| | | | | 35 | | | | | 40 | | | | | 45 |

| Asp | Thr | Glu | Glu | Tyr | Cys | Ala | Ala | Val | Cys | Gly | Ser | Ala |
| | | | | 50 | | | | | 55 | | | 58 |

( 2 ) INFORMATION FOR SEQ ID NO:57:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:57:

| Val | Arg | Glu | Val | Cys | Ser | Gln | Ala | Glu | Pro | Gly | Pro | Cys | Arg |
| 1 | | | | 5 | | | | | 10 | | | | 15 |

| Ala | Leu | Ile | Leu | Arg | Trp | Tyr | Phe | Asp | Val | Thr | Glu | Gly | Lys | Cys |
| | | | | 20 | | | | | 25 | | | | | 30 |

| Ala | Pro | Phe | Phe | Tyr | Gly | Gly | Cys | Tyr | Gly | Asn | Arg | Asn | Asn | Phe |
| | | | | 35 | | | | | 40 | | | | | 45 |

| Asp | Thr | Glu | Glu | Tyr | Cys | Ala | Ala | Val | Cys | Gly | Ser | Ala |
| | | | | 50 | | | | | 55 | | | 58 |

(2) INFORMATION FOR SEQ ID NO:58:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:58:

Gly  Gly  Gly  Gly  Ser
1                     5